(12) United States Patent
Hu

(10) Patent No.: US 7,304,065 B2
(45) Date of Patent: Dec. 4, 2007

(54) MELANIN CONCENTRATING HORMONE ANTAGONISTS

(75) Inventor: Xiufeng Eric Hu, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 515 days.

(21) Appl. No.: 10/949,841

(22) Filed: Sep. 24, 2004

(65) Prior Publication Data

US 2005/0075324 A1 Apr. 7, 2005

Related U.S. Application Data

(60) Provisional application No. 60/536,640, filed on Jan. 15, 2004, provisional application No. 60/507,773, filed on Oct. 1, 2003.

(51) Int. Cl.
| | | |
|---|---|---|
| A61K 31/50 | (2006.01) | |
| A61K 31/501 | (2006.01) | |
| A61K 31/445 | (2006.01) | |
| A61K 31/165 | (2006.01) | |
| A01N 43/40 | (2006.01) | |
| A01N 37/18 | (2006.01) | |
| C07D 211/06 | (2006.01) | |
| C07D 241/04 | (2006.01) | |
| C07D 295/00 | (2006.01) | |

(52) U.S. Cl. .............. 514/252.12; 514/319; 514/617; 546/205; 544/400; 564/161

(58) Field of Classification Search .............. None
See application file for complete search history.

(56) References Cited

U.S. PATENT DOCUMENTS

| 6,310,107 B1 | 10/2001 | Kato et al. |
|---|---|---|
| 6,472,394 B1 | 10/2002 | McKittrick et al. |
| 6,930,185 B2 * | 8/2005 | Ishihara et al. ............ 546/153 |
| 2004/0077628 A1 | 4/2004 | Ishirara et al. |

FOREIGN PATENT DOCUMENTS

| DE | 4438029 A1 | 5/1996 |
|---|---|---|
| DE | 19614718 A1 | 10/1997 |
| EP | 0430459 A1 | 6/1991 |
| EP | 0 540 051 A1 | 5/1993 |
| WO | WO 94/18204 A1 | 8/1994 |
| WO | WO 94/27597 A1 | 12/1994 |
| WO | WO 95/32967 A1 | 12/1995 |
| WO | WO 96/30333 | 10/1996 |
| WO | WO 98/38156 A1 | 9/1998 |
| WO | WO 01/21577 A2 | 3/2001 |
| WO | WO 01/087834 A1 | 11/2001 |
| WO | WO 02/051809 A1 | 7/2002 |
| WO | WO 02/076947 A1 | 10/2002 |
| WO | WO 03/028641 A2 | 4/2003 |
| WO | WO 03/035055 A1 | 5/2003 |
| WO | WO 03/045313 A2 | 6/2003 |
| WO | WO 03/045918 A1 | 6/2003 |
| WO | WO 03/045920 A1 | 6/2003 |
| WO | WO 03/047568 A1 | 6/2003 |
| WO | WO 2004/024702 A1 | 3/2004 |
| WO | WO 2004/037777 A1 | 5/2004 |
| WO | WO 2004/092116 A1 | 10/2004 |

OTHER PUBLICATIONS

Meyers, K., et al., Novel Pyrazolopiperazinone- and Pyrrolopiperazinone-based MCH-R1 Antagonists, Bioorganic & Medicinal Chemistry Letters 17 (2007) 657-661.*
Buhlmayer, P. et al., "Nonpeptidic Angiotensin II Antagonists: Synthesis and In Vitro Activity of a Series of Novel Naphthalene and Tetrahydronapthalene Derivatives", *J. Med. Chem.*, 1991, vol. 34, pp. 3105-3114.
Nakayama, T. et al., "Synthesis and Structure-Activity Study of Protease Inhibitors. II. Amino- and Guanidino-substituted Naphthoates and Tetrahydronaphthoates", Chem. Abstract No. XP002319488, (Database Caplus on line; Accession No. 1985: 112993, abstract.).
Kobayashi, S. et al., "Preparation of sulfonyl moiety-containing heterocyclic compounds as factor Xa inhibitors", Chem. Abstract No. XP002319489, (Database Caplus on line; Accession No. 2000: 133658 (abstract).

* cited by examiner

*Primary Examiner*—James O. Wilson
*Assistant Examiner*—Erich Leeser
(74) *Attorney, Agent, or Firm*—Andrew A. Paul; Kelly L. McDow; Cynthia L. Clay

(57) ABSTRACT

The present invention relates to compounds capable of serving as moderators of human and mammalian appetite and as such provides a means for reducing body mass. The compounds of the present invention are selective against melanin concentrating hormone and do not have the pernicious side effects resulting from compounds which interact with other appetite related brain receptors.

18 Claims, No Drawings

MELANIN CONCENTRATING HORMONE ANTAGONISTS

CROSS REFERENCE TO RELATED APPLICATIONS

This application claims priority under Title 35, United States Code 119(e) from Provisional Application Ser. No. 60/507,773, filed Oct. 1, 2003 and Provisional Application Ser. No. 60/536,640, filed Jan. 15, 2004.

FIELD OF THE INVENTION

The present invention relates to compounds capable of serving as moderators of human and mammalian appetite and as such provides a means for reducing body mass. The compounds of the present invention are selective against melanin concentrating hormone and do not have the pernicious side effects resulting from compounds which interact with other appetite related brain receptors.

BACKGROUND OF THE INVENTION

It has been reported that perhaps 50% of the occidental population and 20% of the oriental population are obese (>20% increase over ideal body mass). In fact, obesity and those having an overweight condition may have reached epidemic proportions in the United States and Western Europe. The Surgeon General of the United States estimated that in 1999 61% of adults were overweight or obese and this number might be as high as 13% for children and adolescents.

In addition to the purely aesthetic reasons for maintaining a proper weight, obesity has a pernicious effect on human health. Excessive body mass has been directly correlated to numerous disease states, inter alia, heart disease, cancer, and type II diabetes.

3-(2-Aminoethyl)-1H-indol-5-ol (serotonin) is a chemical responsible for the regulation of a wide range of CNS brain activity. As a result, extensive research has been conducted in order to understand the role of serotonin and the serotonin (5-HT receptor) in the regulation of a variety of brain-regulated physiological processes from depression to appetite control.

Pharmacologists have long known that direct activation of some 5-HT receptors reduces food consumption.[1] For example, mutant mice that lack the 5-HT$_{2C}$ receptor are obese and activating this receptor in normal rats decreases their eating behavior. One means for treating obesity in humans was the use of fenfluramine in combination with phentermine (fen-phen). However, it was discovered in July 1997 that patients reportedly taking fen-phen developed heart valve disease and fenfluramine was subsequently voluntarily withdrawn from the market.

1. G. Curzon et al., *Trends Pharmacol Sci*, 13, 21-25 (1998).

Following the discovery in 1996 that melanin concentrating hormone (MCH) affects rodent feeding, researchers isolated an orphan G-protein coupled receptor that binds MCH with high affinity. It is now clear that body weight is regulated by both the central nervous system and the peripheral nervous system. Appetite and the associated cravings are CNS controlled while metabolism of food and energy expenditure are peripheral endocrine actions. It is now believed that antagonism of one melanin concentrating hormone receptor (MCH-1R) leads directly to reduction in obesity via reduction in both the desire for food (satiety) and changes in the metabolism of caloric intake (i.e. formation of fat tissue, glycogen conversion, and rate of energy expenditure).

There is therefore a long felt need for a chemical composition of matter which provides a means for controlling appetite and therefore is capable of reducing obesity in humans, said compound acting selectively as a MCH antagonist without having an affinity for the 5-HT receptors.

SUMMARY OF THE INVENTION

The present invention meets the aforementioned needs in that it has been surprisingly discovered that the compounds which comprise the present invention have been found to be effective in controlling appetite, and therefore, obesity and other appetite related disorders. It is also a surprising discovery that the compounds of the present invention have high affinity for MCH-1R receptors but display low or marginal affinity for 5-HT$_{2c}$ receptors.

The present invention encompasses three major aspects each of which have their own separate categories, aspects, iterations, and specific iterative examples. The major aspects of the present invention include:

i) novel compositions of matter which are selective antagonists for MCH-1R receptors over 5-HT$_{2c}$ receptors;

ii) compositions or pharmaceutical compositions (matrices) comprising said compositions of matter, and iii) methods for controlling, abating, preventing, or alleviating the symptoms of diseases or disease states which are controllable by administration of said compositions of matter to a human or mammal, whether said composition of matter is administered alone or in a composition or within a pharmaceutical composition (matrix).

The first aspect of the present invention as a whole, relates to compounds, which include all enantiomeric and diasteriomeric forms and pharmaceutically acceptable salts thereof, said compounds having the formula:

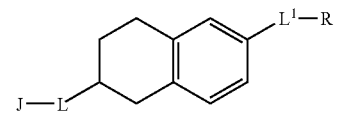

wherein J is a unit containing at least one substituted or unsubstituted aryl or heteroaryl ring;
R is an amino unit having the formula:

$R^1$ and $R^2$ are each independently selected from the group consisting of:
  i) hydrogen;
  ii) —OH;
  iii) substituted or unsubstituted $C_1$-$C_8$ linear, branched or cyclic alkyl;
  iv) substituted or unsubstituted $C_2$-$C_8$ linear, branched or cyclic alkenyl; and v) R¹ and R² can be taken together to form a substituted or unsubstituted heterocyclic, or heteroaryl ring having from 3 to 15 ring atoms;

L and L¹ are linking groups each of which independently has the formula:

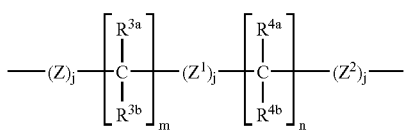

$Z$, $Z^1$, and $Z^2$ are each independently a unit selected from the group consisting of:
  i) $-NR^5-$;
  ii) $-O-$;
  iii) $-SO_2-$;
  iv) $-NR^5SO_2-$; and
  v) $-SO_2NR^5-$;

each of the indices j are independently 0 or 1;
each $R^5$ is independently:
  i) hydrogen; or
  ii) $C_1$-$C_4$ linear, branched, or cyclic alkyl;
$R^{3a}$, $R^{3b}$, $R^{4a}$, and $R^{4b}$ are each independently:
  i) hydrogen;
  ii) hydroxyl;
  iii) halogen;
  iv) $C_1$-$C_4$ linear, branched, or cyclic alkyl,
  v) halogen substituted $C_1$-$C_4$ linear, branched, or cyclic alkyl,
  vi) $C_1$-$C_4$ linear, branched, or cyclic alkoxy,
  vii) $R^{3a}$ and $R^{3b}$ or $R^{4a}$ and $R^{4b}$ can be taken together to form a unit having the formula: C=X wherein X is O, S, or $NR^5$; and
  viii) two $R^{3b}$ or two $R^{4b}$ units from adjacent carbon atoms can be taken together to form a double bond;

the indices m and n are each independently from 0 to 5.

The second major aspect of the present invention relates to pharmaceutical compositions said compositions comprising:
  a) an effective amount of one or more melanin concentrating hormone antagonists according to the present invention; and
  b) one or more pharmaceutically acceptable excipients.

The third major aspect of the present invention relates to methods of use. As described herein below, the compounds of the present invention are effective in controlling appetite in humans or higher mammals, and therefore can serve to control, abate, resolve, or otherwise be used to treat one or more diseases or disease states related to food intake, especially obesity and the diseases which are related to or otherwise caused by or induced by obesity, all of which are accomplished without stimulating CNS or peripheral activity caused by activation of one or more 5-$HT_{2c}$ receptors.

The three major aspects of the present invention encompass the discovery that compounds of the present invention, in addition to selectivity as MCH-1R antagonists, have improved cellular potency and pharmacokinetic properties. This advantage is further exploited in providing a method for controlling obesity and subsequent weight management after weight loss, said method comprising the step of administering to a human or higher mammal an effective amount of a composition comprising one or more of the melanin concentrating hormone antagonists according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to the surprising discovery that certain compounds (compositions of matter, analogs) bind selectively as antagonists to the MCH-1R receptor without substantial binding to the 5-$HT_{2c}$ receptor. What is meant herein by "selective binding" is binding to the MCH-1R receptor at a level at least about 10 fold greater than at the 5-$HT_{2c}$ receptor. For example, a compound with an IC-50 at MCH-1R of 15 nM and an IC-50 at 5-$HT_{2c}$ of >100,000 nM would be a compound which is a selective antagonist at the MCH-1R receptor over the 5-$HT_{2c}$ receptor.

The following chemical hierarchy is used throughout the specification to particularly point out and distinctly claim the units which comprise the compounds of the present invention. The term "hydrocarbyl" stands for any organic molecule, organic functional group, including inorganic atom comprising salts, inter alia, carboxylate salts, quaternary ammonium salts, or for any portion, unit, moiety, and the like, of an organic molecule. Encompassed within the term "hydrocarbyl" are the terms "acyclic" and "cyclic" units which divide hydrocarbyl units into cyclic and non-cyclic families. The family of acyclic units include linear and branched alkyl, alkenyl, alkynyl units and their corresponding connecting units, inter alia, alkylene, alkenylene (—CH=CH—) all of which can be further substituted by the suitable substitutions for hydrogen defined herein below. Encompassed within the family of "cyclic hydrocarbyl" units are the carbocyclic, heterocyclic, aryl, and heteroaryl units, and their corresponding connecting units, inter alia, arylene (e.g., 1,4-phenylene), all of which can be substituted by the suitable substitutions for hydrogen defined herein below. Included within the carbocyclic definition are spirocyclic rings, bicyclic rings, and bridged bicyclic rings, as well as fused rings, inter alia, tetralin. Spirocyclic rings, bicyclic rings, bridged bicyclic rings, and fused rings comprising a heteroatom are divided into categories predicated on the following rules.

For the purposed of the present invention fused ring units, as well as spirocyclic rings, bicyclic rings and the like, which comprise a single heteroatom will be considered to belong to the cyclic family of the heteroatom containing ring. For example, 1,2,3,4-tetrahydroquinoline having the formula:

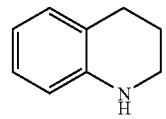

is, for the purposes of the present invention, considered a heterocyclic unit. 6,7-Dihydro-5H-[1]pyrindine having the formula:

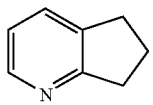

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

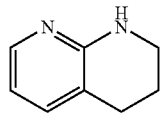

is, for the purposes of the present invention, considered a heteroaryl unit.

The compounds of the present invention comprise linking units. Linking units can be taken together with a substituted or unsubstituted cyclic hydrocarbyl unit to form a single common chemical moiety. For example, a methylene linker and a phenyl unit when taken together is referred to by the artisan of ordinary skill as a benzyl unit, having the formula:

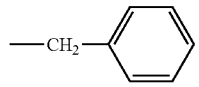

and which is known herein as an "alkylenearyl unit. Likewise a heteroaryl unit taken together with a methylene is defined herein by the term "alkyleneheteroaryl" (e.g. a 2-picolyl unit) having the formula:

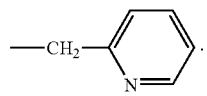

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing, include one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like.

The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

Although the hydrogen atoms of hydrocarbyl units may be substituted by any unit, the following are non-limiting examples of units which can substitute for a hydrogen atom on a hydrocarbyl unit whether cyclic or acyclic:

i) —$[C(R^6)_2]_p(CH=CH)_qR^6$; wherein p is from 0 to 12; q is from 0 to 12;
ii) —$C(X)R^6$;
iii) —$C(O)OR^6$
iv) —$C(X)CH=CH_2$;
v) —$C(X)N(R^6)_2$;
vi) —$C(X)NR^6N(R^6)_2$;
vii) —CN;
viii) —C(O)OM
ix) —$CF_3$, —$CCl_3$, —$CBr_3$;
x) —$N(R^6)_2$;
xi) -halogen;
xii) —$NR^6C(X)R^6$;
xiii) —$NR^6C(X)N(R^6)_2$;
xiv) —$NR^6N(R^6)_2$;
xv) —$NHOR^6$;
xvi) —$OCF_3$, —$OCCl_3$, —$OCBr_3$;
xvii) —$NO_2$;
xviii) —$OR^6$;
xix) —$NR^6S(O)_2R^6$
xx) —$NR^6S(O)_2NR^6$
xxi) —$SO_2N(R^6)_2$
xxii) —$SO_2R^6$
xxiii) —$SO_3M$;
xxiv) —$OSO_3M$;
xxv) —$OP(O)(OM)_2$;
xxvi) —$P(O)(OR^6)_2$
xxvii) —$P(O)(OM)_2$
xxiii) —$OP(O)(OR^6)_2$
xxix) and mixtures thereof wherein $R^6$ is hydrogen, substituted or unsubstituted $C_1$-$C_{20}$ linear, branched, or cyclic alkyl, $C_6$-$C_{20}$ aryl, $C_7$-$C_{20}$ alkylenearyl, and mixtures thereof; M is hydrogen, or a salt forming cation; X is =O, =S, =$NR^6$, and mixtures thereof.

Melanin Concentrating Hormone Antagonists

The compounds of the present invention are melanin concentrating hormone antagonists and comprise all enantiomeric and diasteriomeric forms and pharmaceutically acceptable salts thereof, said antagonists having the principal 1,2,3,4-tetrahydronaphthalene scaffold with the formula:

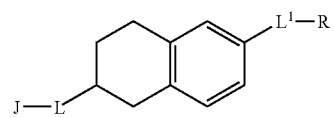

wherein said melanin concentrating hormone antagonists have three principal parts:

a) a core 2,6-disubstituted 1,2,3,4-tetrahydronaphthalene unit having the formula:

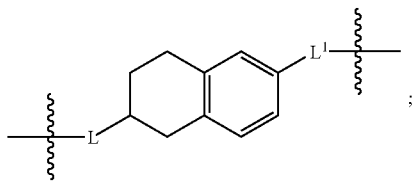

b) aryl or heteroaryl containing J units wherein J is a unit chosen from:
  i) units comprising two rings having the formula:

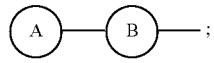

or
  ii) units comprising one ring having the formula:

wherein A and B are defined herein below; and
c) an amino unit comprising a basic nitrogen atom having the formula:

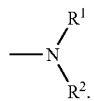

First Category of Aryl or Heteroaryl Containing Units

The aryl and heteroaryl containing units are attached to the core 1,2,3,4-tetrahydro-naphthalene scaffold at the 2-position of the ten atom ring. The first category of aryl or heteroaryl containing units are two ring units having the formula:

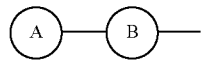

wherein A and B are rings independently selected from carbocyclic, aryl, heterocyclic, and heteroaryl, provided at least one ring is chosen from aryl or heteroaryl.

Aspect 1 of this category relates to units having no substitutions for the hydrogen atoms on the aryl or heteroaryl ring.

The first iteration of Aspect 1 of Category 1 of aryl or heteroaryl containing units relates to 4-biphenyl having the formula:

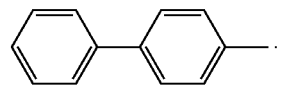

The second iteration of Aspect 1 of Category 1 of aryl or heteroaryl containing units relates to units comprising an A ring heteroaryl unit and a B ring aryl unit, for example, the 4-pyridin-4-ylphenyl unit having the formula:

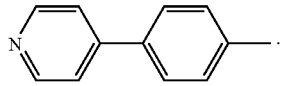

Further non limiting examples of the second iteration of Aspect 1 includes 4-pyridin-2-ylphenyl, 4-pyridin-3-ylphenyl, 4-pyrimidin-2-ylphenyl, 4-pyrimidin-4-ylphenyl, 4-pyrimidin-5-yl-phenyl, 3-pyridin-2-ylphenyl, 3-pyridin-3-ylphenyl, 3-pyrimidin-2-ylphenyl, 3-pyrimidin-4-ylphenyl, and 3-pyrimidin-5-yl-phenyl.

Aspect 2 of this category relates to units having one or more substitutions for hydrogen atoms on the A ring, for example, units having the formula:

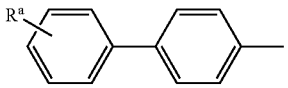

wherein $R^a$ represents one or more substitutions for hydrogen atoms on the A ring aryl unit.

The first iteration of Aspect 2 relates to units having the formula:

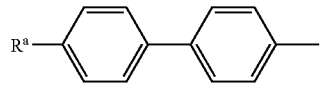

wherein $R^a$ is chosen from:
  i) fluoro;
  ii) chloro;
  iii) —$NO_2$;
  iv) —CN;
  v) —OH;
  vi) —$NH_2$;
  vii) —$N(CH_3)_2$;
  viii) —$OCH_3$;
  ix) —$NHC(O)CH_3$;
  x) —$C(O)OR^7$;
  xi) —$CF_3$; and
  xii) $C_1$-$C_4$ linear, branched, or cyclic alkyl;
  $R^7$ is hydrogen, $C_1$-$C_{10}$ linear, branched, or cyclic alkyl.

Non-limiting examples of the first iteration of Aspect 2 include 4'-fluoro-biphenyl, 4'-chloro-biphenyl, 4'-nitro-biphenyl, 4'-cyano-biphenyl, 4'-hydroxy-biphenyl, 4'-methoxy-biphenyl, 4'-trifluoromethyl-biphenyl, and 4'-methyl-biphenyl.

The second iteration of Aspect 2 of Category 1 of aryl or heteroaryl containing units relates to 3'-substituted-biphenyl units wherein $R^a$ is the same as defined herein above for the first iteration of Aspect 2. Non-limiting examples of the second iteration of Aspect 2 include 3'-fluoro-biphenyl, 3'-chloro-biphenyl, 3'-nitro-biphenyl, 3'-cyano-biphenyl, 3'-hydroxy-biphenyl, 3'-methoxy-biphenyl, 3'-trifluoromethyl-biphenyl, and 3'-methyl-biphenyl.

The third iteration of Aspect 2 of Category 1 of aryl or heteroaryl containing units relates to 2'-substituted-biphenyl units wherein $R^a$ is the same as defined herein above for the first iteration of Aspect 2. Non-limiting examples of the third iteration of Aspect 2 include 2'-fluoro-biphenyl, 2'-chloro-biphenyl, 2'-nitro-biphenyl, 2'-cyano-biphenyl, 2'-hydroxy-biphenyl, 2'-methoxy-biphenyl, 2'-trifluoromethyl-biphenyl, and 2'-methyl-biphenyl.

The fourth iteration of Aspect 2 of Category 1 of aryl or heteroaryl containing units relates to A ring di-substituted-biphenyl units wherein $R^a$ is the same as defined herein above for the first iteration of Aspect 2. Non-limiting examples of the fourth iteration of Aspect 2 include 2',4'-difluoro-biphenyl, 2',4'-dichloro-biphenyl, 2',4'-dinitro-biphenyl, 2',4'-dicyano-biphenyl, 2',4'-dihydroxy-biphenyl, 2',4'-dimethoxy-biphenyl, 2',4'-ditrifluoromethyl-biphenyl, 2',4'-dimethyl-biphenyl, 3',4'-difluoro-biphenyl, 3',4'-dichloro-biphenyl, 3',4'-dinitro-biphenyl, 3',4'-dicyano-biphenyl, 3',4'-dihydroxy-biphenyl, 3',4'-dimethoxy-biphenyl, 3',4'-ditrifluoromethyl-biphenyl, 3',4'-dimethyl-biphenyl, 3',5'-difluoro-biphenyl, 3',5'-dichloro-biphenyl, 3',5'-dinitro-biphenyl, 3',5'-dicyano-biphenyl, 3',5'-dihydroxy-biphenyl, 3',5'-dimethoxy-biphenyl, 3',5'-ditrifluoromethyl-biphenyl, 3',5'-dimethyl-biphenyl, 2'-fluoro-4'-methyl-biphenyl, 2'-chloro-3'-methyl-biphenyl, 2'-methyl-3'-chloro-biphenyl, 2'-cyano-4'-fluoro-biphenyl, and 2'-methyl-4'-hydroxy-biphenyl.

Aspect 3 of this category relates to units having a heteroaryl or heterocyclic A ring, said units having the formula:

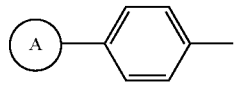

wherein A is a substituted or unsubstituted heterocyclic or heteroaryl ring chosen from pyridinyl, pyrimidinyl, triazinyl, piperidinyl, piperazinyl, morpholinyl, furanyl, thiophenyl, pyrrolyl, pyrazolyl, imidazolyl, [1,2,3]triazolyl, [1,2,4]triazolyl, isoxazolyl, oxazolyl, and thiazolyl.

Other aspects of Category 1 of aryl or heteroaryl containing units include:
  i) units wherein one or more hydrogen atoms of a heteroaryl or heterocyclic A ring, for example, units which comprise Aspect 3 above, are substituted by one or more $R^a$ units as defined herein above;
  ii) units wherein one or more hydrogen atoms of an A ring and a heteroaryl B ring are substituted by one or more $R^a$ units;
  iii) units wherein one or more hydrogen atoms of a heteroaryl A ring are substituted by one or more $R^a$ units as defined herein above; and
  iv) units wherein the A ring is a heterocyclic ring and the B ring is an aryl ring either of which can be substituted with one or more $R^a$ units.

Second Category of Aryl or Heteroaryl Containing Units

The second category of aryl or heteroaryl containing units has the formula:

wherein A is a substituted or unsubstituted aryl or heteroaryl unit.

Aspect 1 of this category relates to units having a single substitution for hydrogen on a phenyl ring, said units having the formula:

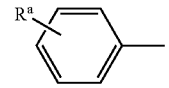

wherein $R^a$ is chosen from:
  i) fluoro;
  ii) chloro;
  iii) —$NO_2$;
  iv) —CN;
  v) —OH;
  vi) —$CF_3$; and
  vii) $C_1$-$C_4$ linear, branched, or cyclic alkyl.

Aspect 2 of this category relate to units having a single substitution for hydrogen on a heteroaryl ring, for example, units having the formula:

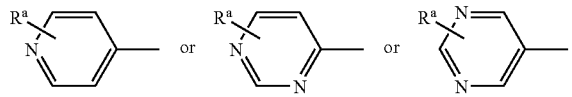

wherein $R^a$ is the same as defined herein above for Aspect 1 of this category.

Amino Units Comprising a Basic Nitrogen Atom

A third principal element of the MCH antagonists of the present invention relates to the R amino units comprising a basic nitrogen atom having the formula:

which is linked to the core 1,2,3,4-tetrahydronaphthalene unit by a $L^1$ linking unit.

$R^1$ and $R^2$ are each independently chosen from:
  i) hydrogen;
  ii) $C_1$-$C_8$ substituted or unsubstituted linear, branched, or cyclic hydrocarbyl;
  iii) substituted or unsubstituted aryl; or $R^1$ and $R^2$ can be taken together to form a substituted or unsubstituted heterocyclic ring having from 3 to 8 atoms.

Aspect 1 of R units relates to units wherein $R^1$ and $R^2$ are each independently hydrogen or $C_1$-$C_8$ linear hydrocarbyl.

The first iteration of Aspect 1 relates to $R^1$ and $R^2$ are each independently chosen from hydrogen, methyl, and ethyl.

This iteration includes amino units chosen from —NH$_2$, —NH(CH$_3$), —NH(CH$_2$CH$_3$), —N(CH$_3$)$_2$, —N(CH$_3$)(CH$_2$CH$_3$), and —N(CH$_2$CH$_3$)$_2$.

Other iterations of this aspect include alkyl units having more than three carbon atoms, for example, —NH[CH(CH$_3$)$_2$] and —N[CH(CH$_3$)$_2$]$_2$.

Aspect 2 of R units relates to units wherein R$^1$ and R$^2$ are taken together to form a heterocyclic ring having from 3 to 8 atoms. Non-limiting examples of rings which can be formed from R$^1$ and R$^2$ include: aziridin-1-yl, azetidin-1-yl, pyrrolidin-1-yl, 3-pyrrolin-1-yl, imidazolidin-1-yl, pyrazolidin-1-yl, piperidine-1-yl, piperazin-1-yl, 4-substituted-piperazin-1-yl, azepan-1-yl, and morpholin-4-yl.

Iterations of Aspect 2 relate to the value or Y as described herein below and include substituted or unsubstituted heterocyclic units having the formula:

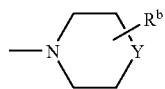

R$^b$ represents one or more substitutions for hydrogen as defined herein above; Y is —C(R$^8$)$_2$—, —NR$^8$—, —O—, or —S—; R$^8$ is substituted or unsubstituted C$_1$-C$_8$ alkyl, substituted or unsubstituted aryl, or substituted or unsubstituted heteroaryl.

Non-limiting examples of R units which comprise the first iteration of Aspect 2 wherein Y is —C(R$^8$)$_2$— are units chosen from piperidine, 2-methylpiperidine, 3-piperidine, 4-methyl-piperidine, and 2,6-dimethylpiperidine.

Non-limiting examples of R units which comprise the second iteration of Aspect 2 wherein Y is —NR$^8$— are units chosen from piperazine, 4-methylpiperazin-1-yl, 4-phenylpiperazin-1-yl, 4-(2-hydroxyethyl)-piperazin-1-yl, 4-(2-fluorophenyl)piperazin-1-yl, and 4-(3-trifluoro-methyl)phenylpiperazin-1-yl.

Non-limiting examples of R units which comprise the third iteration of Aspect 2 wherein Y is —O— include morpholin-4-yl, 2,6-dimethylmorpholin-4-yl, and the like.

Core 1,2,3,4,-Tetrahydronaphthylene Units

The third principal element of the MCH antagonists of the present invention is the core 2,6-disubstituted 1,2,3,4-tetrahydronaphthalene unit having the formula:

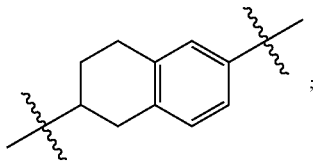

which when taken together with the linking groups L and L$^1$ as defined herein below, form the core 1,2,3,4-tetrahydronaphthalene scaffold with the formula:

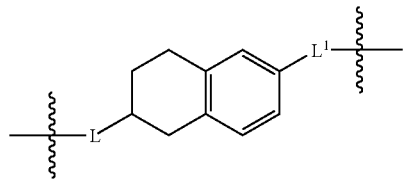

Linking Units

L and L$^1$ are linking groups which serve to tether the J and R units to the core tetrahydronaphthalene ring scaffold, as well as linking the A and B rings which comprise the J units of the present invention. Each L and L$^1$ is independently selected and is defined by the formula:

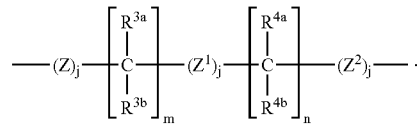

Z, Z$^1$, and Z$^2$ are heteroatom comprising units and are each independently selected from the group consisting of:
i) —NR$^5$—;
ii) —O—;
iii) —SO$_2$—;
iv) —NR$^5$SO$_2$—; and
v) —SO$_2$NR$^5$—;

and for each of Z, Z$^1$, and Z$^2$, the index j is independently 0 or 1. When j is 0 a particular Z, Z$^1$, or Z$^2$ is absent, when j is 1 the Z, Z$^1$, or Z$^2$ unit is present.

For the above Z, Z$^1$, and Z$^2$ units, each R$^5$ is independently:
i) hydrogen; or
ii) C$_1$-C$_4$ linear, branched, or cyclic alkyl.

The units R$^{3a}$, R$^{3b}$, R$^{4a}$, and R$^{4b}$ are each attached to a carbon atom and each independently are selected from the group consisting of:
i) hydrogen;
ii) hydroxyl;
iii) halogen;
iv) C$_1$-C$_4$ linear, branched, or cyclic alkyl,
v) halogen substituted C$_1$-C$_4$ linear, branched, or cyclic alkyl,
vi) C$_1$-C$_4$ linear, branched, or cyclic alkoxy,
vii) R$^{3a}$ and R$^{3b}$ or R$^{4a}$ and R$^{4b}$ can be taken together to form a unit having the formula: C=X wherein X is O, S, or NR$^5$; and
viii) two R$^{3b}$ or two R$^{4b}$ units from adjacent carbon atoms can be taken together to form a double bond;
the indices m and n are each independently from 0 to 5.

The first aspect of the core units of the present invention relate to scaffolds having the formula:

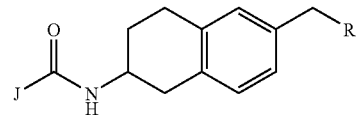

wherein L is a unit having the formula:

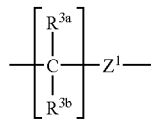

wherein $R^{3a}$ and $R^{3b}$ are taken together to form a carbonyl unit, C=O, and the unit $Z^1$ has the formula —$NR^5$— wherein $R^5$ is hydrogen; $L^1$ has the formula:

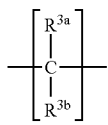

wherein $R^{3a}$ and $R^{3b}$ are each hydrogen.

The second aspect of the core units of the present invention relate to scaffolds having the formula:

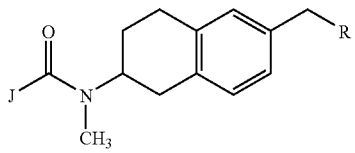

wherein L is a unit having the formula:

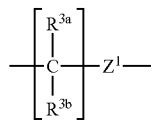

wherein $R^{3a}$ and $R^{3b}$ are taken together to form a carbonyl unit, C=O, and the unit $Z^1$ has the formula —$NR^5$— wherein $R^5$ is methyl; $L^1$ has the formula:

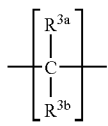

wherein $R^{3a}$ and $R^{3b}$ are each hydrogen.

The third aspect of the core units of the present invention relate to scaffolds having the formula:

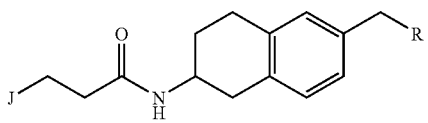

wherein L is a unit having the formula:

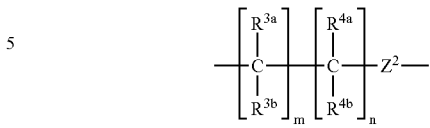

wherein the index m is equal to 2, thereby two units comprising $R^{3a}$ and $R^{3b}$ are present, and all of the $R^{3a}$ and $R^{3b}$ units are hydrogen; the index n is equal to 1, $R^{4a}$ and $R^{4b}$ are taken together to form a carbonyl unit, C=O, and the unit $Z^2$ has the formula —$NR^5$— wherein $R^5$ is hydrogen, (Z and $Z^1$ are absent, their respective indices j equal to 0); $L^1$ has the formula:

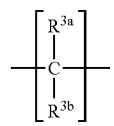

wherein $R^{3a}$ and $R^{3b}$ are each hydrogen.

Analog Categories

The analogs (compounds) of the present invention are arranged in several categories to assist the formulator in applying a rational synthetic strategy for the preparation of analogs which are not expressly exampled herein. The arrangement into categories does not imply increased or decreased efficacy or utility for any of the compositions of matter, compositions, or methods described herein.

Category I of the present invention relates to compounds with a core scaffold having the formula:

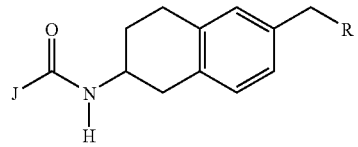

The first aspect of Category I relates to $R^a$-substituted-biphenyl-4-carboxylic acid (6-aminomethyl-1,2,3,4-tetrahydro-naphthalen-2-yl)-amides having the formula:

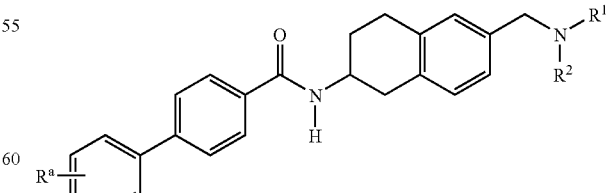

wherein $R^1$ and $R^2$ are each independently hydrogen or $C_1$-$C_3$ linear or branched alkyl, and the $R^a$ substituted biphenyl units are defined herein in Table 1.

TABLE I

| No. | R$^a$ containing unit | R$^1$ | R$^2$ |
|---|---|---|---|
| 1 | 4'-fluoro-4-biphenyl | —H | —H |
| 2 | 4'-fluoro-4-biphenyl | —H | —CH$_3$ |
| 3 | 4'-fluoro-4-biphenyl | —H | —CH$_2$CH$_3$ |
| 4 | 4'-fluoro-4-biphenyl | —H | —CH$_2$CH$_2$CH$_3$ |
| 5 | 4'-fluoro-4-biphenyl | —H | —CH(CH$_3$)$_2$ |
| 6 | 4'-fluoro-4-biphenyl | —CH$_3$ | —CH$_3$ |
| 7 | 4'-fluoro-4-biphenyl | —CH$_3$ | —CH$_2$CH$_3$ |
| 8 | 4'-fluoro-4-biphenyl | —CH$_3$ | —CH$_2$CH$_2$CH$_3$ |
| 9 | 4'-fluoro-4-biphenyl | —CH$_3$ | —CH(CH$_3$)$_2$ |
| 10 | 4'-fluoro-4-biphenyl | —CH$_2$CH$_3$ | —CH$_2$CH$_3$ |
| 11 | 4'-fluoro-4-biphenyl | —CH$_2$CH$_3$ | —CH$_2$CH$_2$CH$_3$ |
| 12 | 4'-fluoro-4-biphenyl | —CH$_2$CH$_3$ | —CH(CH$_3$)$_2$ |
| 13 | 2',4'-difluoro-4-biphenyl | —H | —H |
| 14 | 2',4'-difluoro-4-biphenyl | —H | —CH$_3$ |
| 15 | 2',4'-difluoro-4-biphenyl | —H | —CH$_2$CH$_3$ |
| 16 | 2',4'-difluoro-4-biphenyl | —H | —CH$_2$CH$_2$CH$_3$ |
| 17 | 2',4'-difluoro-4-biphenyl | —H | —CH(CH$_3$)$_2$ |
| 18 | 2',4'-difluoro-4-biphenyl | —CH$_3$ | —CH$_3$ |
| 19 | 2',4'-difluoro-4-biphenyl | —CH$_3$ | —CH$_2$CH$_3$ |
| 20 | 2',4'-difluoro-4-biphenyl | —CH$_3$ | —CH$_2$CH$_2$CH$_3$ |
| 21 | 2',4'-difluoro-4-biphenyl | —CH$_3$ | —CH(CH$_3$)$_2$ |
| 22 | 2',4'-difluoro-4-biphenyl | —CH$_2$CH$_3$ | —CH$_2$CH$_3$ |
| 23 | 2',4'-difluoro-4-biphenyl | —CH$_2$CH$_3$ | —CH$_2$CH$_2$CH$_3$ |
| 24 | 2',4'-difluoro-4-biphenyl | —CH$_2$CH$_3$ | —CH(CH$_3$)$_2$ |
| 25 | 4'-cyano-4-biphenyl | —H | —H |
| 26 | 4'-cyano-4-biphenyl | —H | —CH$_3$ |
| 27 | 4'-cyano-4-biphenyl | —H | —CH$_2$CH$_3$ |
| 28 | 4'-cyano-4-biphenyl | —H | —CH$_2$CH$_2$CH$_3$ |
| 29 | 4'-cyano-4-biphenyl | —H | —CH(CH$_3$)$_2$ |
| 30 | 4'-cyano-4-biphenyl | —CH$_3$ | —CH$_3$ |
| 31 | 4'-cyano-4-biphenyl | —CH$_3$ | —CH$_2$CH$_3$ |
| 32 | 4'-cyano-4-biphenyl | —CH$_3$ | —CH$_2$CH$_2$CH$_3$ |
| 33 | 4'-cyano-4-biphenyl | —CH$_3$ | —CH(CH$_3$)$_2$ |
| 34 | 4'-cyano-4-biphenyl | —CH$_2$CH$_3$ | —CH$_2$CH$_3$ |
| 35 | 4'-cyano-4-biphenyl | —CH$_2$CH$_3$ | —CH$_2$CH$_2$CH$_3$ |
| 36 | 4'-cyano-4-biphenyl | —CH$_2$CH$_3$ | —CH(CH$_3$)$_2$ |
| 37 | 4'-chloro-4-biphenyl | —H | —H |
| 38 | 4'-chloro-4-biphenyl | —H | —CH$_3$ |
| 39 | 4'-chloro-4-biphenyl | —H | —CH$_2$CH$_3$ |
| 40 | 4'-chloro-4-biphenyl | —H | —CH$_2$CH$_2$CH$_3$ |
| 41 | 4'-chloro-4-biphenyl | —H | —CH(CH$_3$)$_2$ |
| 42 | 4'-chloro-4-biphenyl | —CH$_3$ | —CH$_3$ |
| 43 | 4'-chloro-4-biphenyl | —CH$_3$ | —CH$_2$CH$_3$ |
| 44 | 4'-chloro-4-biphenyl | —CH$_3$ | —CH$_2$CH$_2$CH$_3$ |
| 45 | 4'-chloro-4-biphenyl | —CH$_3$ | —CH(CH$_3$)$_2$ |
| 46 | 4'-chloro-4-biphenyl | —CH$_2$CH$_3$ | —CH$_2$CH$_3$ |
| 47 | 4'-chloro-4-biphenyl | —CH$_2$CH$_3$ | —CH$_2$CH$_2$CH$_3$ |
| 48 | 4'-chloro-4-biphenyl | —CH$_2$CH$_3$ | —CH(CH$_3$)$_2$ |
| 49 | 4'-methoxy-4-biphenyl | —H | —H |
| 50 | 4'-methoxy-4-biphenyl | —H | —CH$_3$ |
| 51 | 4'-methoxy-4-biphenyl | —H | —CH$_2$CH$_3$ |
| 52 | 4'-methoxy-4-biphenyl | —H | —CH$_2$CH$_2$CH$_3$ |
| 53 | 4'-methoxy-4-biphenyl | —H | —CH(CH$_3$)$_2$ |
| 54 | 4'-methoxy-4-biphenyl | —CH$_3$ | —CH$_3$ |
| 55 | 4'-methoxy-4-biphenyl | —CH$_3$ | —CH$_2$CH$_3$ |
| 56 | 4'-methoxy-4-biphenyl | —CH$_3$ | —CH$_2$CH$_2$CH$_3$ |
| 57 | 4'-methoxy-4-biphenyl | —CH$_3$ | —CH(CH$_3$)$_2$ |
| 58 | 4'-methoxy-4-biphenyl | —CH$_2$CH$_3$ | —CH$_2$CH$_3$ |
| 59 | 4'-methoxy-4-biphenyl | —CH$_2$CH$_3$ | —CH$_2$CH$_2$CH$_3$ |
| 60 | 4'-methoxy-4-biphenyl | —CH$_2$CH$_3$ | —CH(CH$_3$)$_2$ |
| 61 | 4'-trifluoromethyl-4-biphenyl | —H | —H |
| 62 | 4'-trifluoromethyl-4-biphenyl | —H | —CH$_3$ |
| 63 | 4'-trifluoromethyl-4-biphenyl | —H | —CH$_2$CH$_3$ |
| 64 | 4'-trifluoromethyl-4-biphenyl | —H | —CH$_2$CH$_2$CH$_3$ |
| 65 | 4'-trifluoromethyl-4-biphenyl | —H | —CH(CH$_3$)$_2$ |
| 66 | 4'-trifluoromethyl-4-biphenyl | —CH$_3$ | —CH$_3$ |
| 67 | 4'-trifluoromethyl-4-biphenyl | —CH$_3$ | —CH$_2$CH$_3$ |
| 68 | 4'-trifluoromethyl-4-biphenyl | —CH$_3$ | —CH$_2$CH$_2$CH$_3$ |
| 69 | 4'-trifluoromethyl-4-biphenyl | —CH$_3$ | —CH(CH$_3$)$_2$ |
| 70 | 4'-trifluoromethyl-4-biphenyl | —CH$_2$CH$_3$ | —CH$_2$CH$_3$ |
| 71 | 4'-trifluoromethyl-4-biphenyl | —CH$_2$CH$_3$ | —CH$_2$CH$_2$CH$_3$ |
| 72 | 4'-trifluoromethyl-4-biphenyl | —CH$_2$CH$_3$ | —CH(CH$_3$)$_2$ |

The compounds which comprise Category I of the present invention can be suitably prepared by the procedures outlined herein below in Scheme I and Scheme II.

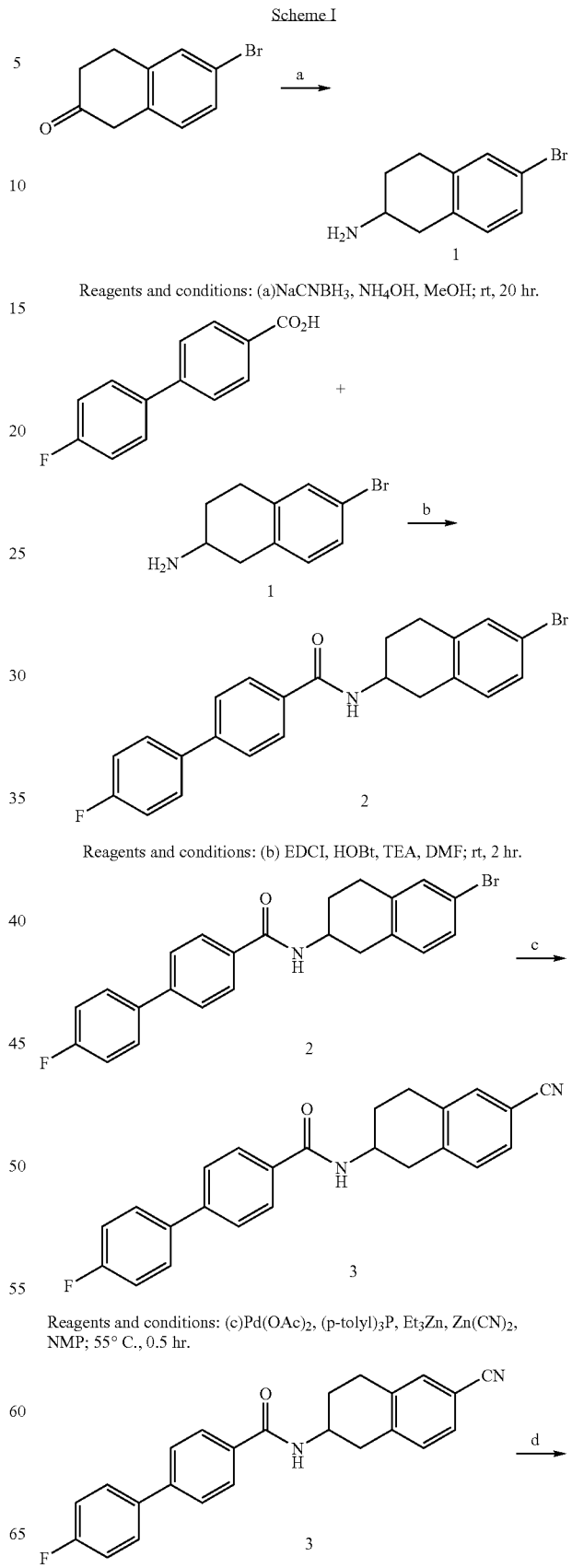

Scheme I

Reagents and conditions: (a) NaCNBH$_3$, NH$_4$OH, MeOH; rt, 20 hr.

Reagents and conditions: (b) EDCI, HOBt, TEA, DMF; rt, 2 hr.

Reagents and conditions: (c) Pd(OAc)$_2$, (p-tolyl)$_3$P, Et$_2$Zn, Zn(CN)$_2$, NMP; 55° C., 0.5 hr.

-continued

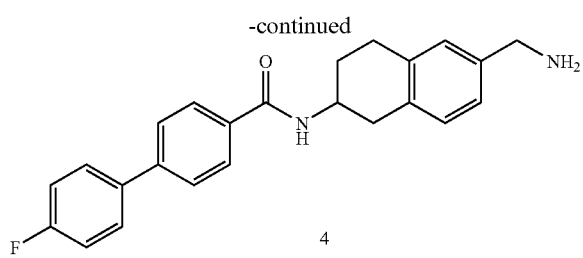

4

Reagents and conditions:(d) H₂, Raney Ni, NH₄OH, DMF; rt, 18 hr.

EXAMPLE 1

Preparation of 4'-fluoro-biphenyl-4-carboxylic acid (6-aminomethyl-1,2,3,4-tetrahydro-naphthalen-2-yl)-amide (4)

Preparation of 6-bromo-1,2,3,4-tetrahydro-naphthalen-2-ylamine (1)

This material is commercially available, however, it can be successfully prepared by the following procedure. To a solution of the 6-bromo 2-tetralone (0.288 g, 1.280 mmol) and NH₄OAc (0.986 g, 10 eq.) in MeOH (40 mL) is added NaCNBH₃ (0.097 g, 1.2 eq) at room temperature. The resulting yellow solution is stirred at that temperature for 20 hours, then acidified with 0.1 M HCl to pH 2.0. The mixture is extracted with CH₂Cl₂ twice. The aqueous layer is basified with 1.0 N NaOH to pH 10 then extracted with CH₂Cl₂ three times. The extracts are dried over anhydrous MgSO₄ and concentrated in vacuo to afford 0.8 g (44% yield) of the desired product as a yellow oil which is used without further purification. ¹H NMR (300 MHz, CD₃OD) δ 7.27-7.35 (m, 8H), 7.05 (d, J=8.4 Hz, 4H), 3.56 (m, 1H), 3.17 (dd, J=3.9, 16.2 Hz, 1H), 2.95 (m, 2H), 2.81 (dd, J=9.9, 16.2 Hz, 1H), 2.19-2.29 (m, 1H), 1.79-1.92 (m, 1H); ¹³C NMR (75 MHz, CD₃OD) δ 137.3, 131.5, 131.4, 130.9, 120.1, 47.4, 26.9, 26.7; LRMS: 226.1 (M+H), 209 (M+H−NH3).

Preparation of 4'-fluoro-biphenyl-4-carboxylic acid (6-bromo-1,2,3,4-tetrahydro-naphthalen-2-yl)-amide (2)

A solution of 6-bromo-1,2,3,4-tetrahydro-naphthalen-2-ylamine trifluoroacetate salt, 1, (0.222 g, 0.661 mmol), 4'-fluoro-phenyl-4-benzoic acid (0.21 g, 1.5 eq.), 1-hydroxybenzotriazole (0.134 g, 1.5 eq.), triethylamine (0.187 mL, 2 eq.), and 1-(3-dimethyl-aminopropyl)-3-ethylcarbodiimide (0.189 g, 1.5 eq.) in DMF (5 mL) is stirred at room temperature for 2 hours. The mixture is then diluted with EtOAc, washed with saturated NaHCO₃, dried over anhydrous MgSO₄ and concentrated in vacuo to leave a crude residue which is triturated with MeOH to afford 0.312 g, (75% yield) of the desired product as a white solid. ¹H NMR (300 MHz, THF-D8) δ 7.93 (d, J=8.4 Hz, 2H), 7.65 (d, J=8.4 Hz, 2H), 7.65-7.71 (m, 2H), 7.60 (d, J=6.6 Hz, 1H), 6.90-7.32 (m, 5H), 4.40 (m, 1H), 3.16 (dd, J=5.1, 16.5 Hz, 1H), 2.94 (m, 1H), 2.70-2.81 (m, 2H), 2.14-2.26 (m, 1H), 1.80-2.92 (m, 1H); ¹⁹F NMR (282 MHz, THF-D8) δ 46.9; ¹³C NMR (75 MHz, THF-D8) δ 166.0, 165.8, 162.2, 142.8, 139.0, 137.0, 135.0, 131.8, 131.4, 129.3, 129.1, 128.3, 126.8, 119.7, 116.1, 115.8, 46.3, 35.5, 29.3, 28.5; LRMS: 424.1 (M+H).

Preparation of 4'-fluoro-biphenyl-4-carboxylic acid (6-cyano-1,2,3,4-tetrahydro-naphthalen-2-yl)-amide (3)

A degassed solution of Pd(OAc)₂ (0.078 g, 0.35 mmol) and tri-o-tolylphosphine (0.422 g, 1.39 mmol) in N-methylpyrrolidinone (5 mL) is heated at 55° C. for 30 minutes under a nitrogen atmosphere. To this solution is added diethyl zinc(II) (1.0M in hexane, 0.69 mL, 0.69 mmol) and the mixture is maintained at 55° C. for an additional 30 minutes. A premixed solution of 4'-fluoro-biphenyl-4-carboxylic acid (6-bromo-1,2,3,4-tetrahydro-naphthalen-2-yl)-amide, 2, (1.470 g, 3.464 mmol) and Zn(CN)₂ (0.405 g, 3.46 mmol) in N-methyl pyrrolidinone (5 mL) is added to the above mixture via cannula. The reaction mixture is then heated at 60° C. overnight. Once cooled, the desired product is then precipitated by adding MeOH to afford 1.43 g (quantitative yield) of an off-white solid. ¹H NMR (300 MHz, DMF-D7) δ 8.78 (d, J=7.5 Hz, 1H), 8.28 (d, J=8.7 Hz, 2H), 7.98-8.04 (m, 4H), 7.76-7.81 (m, 2H), 7.55 (d, J=8.7 Hz, 2H), 7.51-7.54 (m, 1H), 4.56 (m, 1H), 3.42-3.50 (m, 1H), 3.16-3.24 (m, 3H), 2.32-2.42 (m, 1H), 2.06-2.20 (m, 1H); ¹³C NMR (75 MHz, DMF-D7) δ 166.2, 162.6, 142.3, 142.0, 138.1, 134.2, 132.8, 130.7, 129.5, 129.4, 128.4, 126.9, 119.8, 116.3, 116.0, 109.7, 45.9, 30.4, 28.7, 28.0; LRMS: 371.3 (M+H).

Preparation of 4'-fluoro-biphenyl-4-carboxylic acid (6-aminomethyl-1,2,3,4-tetrahydro-naphthalen-2-yl)-amide (4)

A suspension of 4'-fluoro-biphenyl-4-carboxylic acid (6-cyano-1,2,3,4-tetrahydro-naphthalen-2-yl)-amide, 3, (1.430 g, 3.514 mmol), Raney-Ni (0.5 g) and 28% NH₄OH (1.0 mL) in DMF (25 mL) is hydrogenated for 18 hours. The catalyst is removed by filtration and the filtrate concentrated in vacuo to afford 1.352 g (94% yield) of the desired product. ¹H NMR (300 MHz, DMF-D7) δ 8.55 (d, J=7.5 Hz, 1H), 8.20 (d, J=8.7 Hz, 2H), 7.72-7.85 (m, 4H), 7.35 (t, J=9.3 Hz, 2H), 6.95-7.23 (br, 3H), 4.20-4.42 (m, 1H), 3.12-3.24 (br, 2H), 2.90-3.08 (m, 4H), 2.11-2.25 (m, 1H), 1.90 (m, 1H); ¹³C NMR (75 MHz, DMF-D7) δ166.2, 164.8, 142.6, 136.8, 135.8, 134.5, 133.8, 129.6, 129.4, 129.3, 128.5, 127.0, 125.6, 116.4, 116.1, 64.0, 46.9, 34.2, 28.7, 28.0; ¹⁹F NMR (282 MHz, DMF-D7) δ 46.6; LRMS: 375.3 (M+H), 358.3 (M+H−NH3), HRMS: calcd: for C₂₄H₂₄FN₂O 375.1873, found: 375.1866.

Scheme II

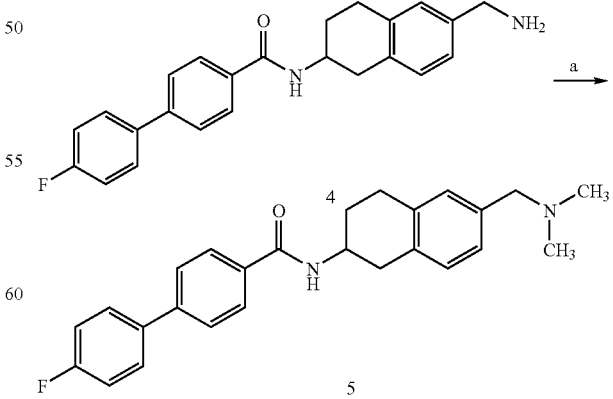

Reagents and conditions: (a) NaBH(OAc)₃, HCHO, DMF; rt. 20 hr.

EXAMPLE 2

Preparation of 4'-fluoro-biphenyl-4-carboxylic acid (6-dimethylaminomethyl-1,2,3,4-tetrahydro-naphthalen-2-yl)-amide (5)

A solution of 4'-fluoro-biphenyl-4-carboxylic acid (6-aminomethyl-1,2,3,4-tetrahydro-naphthalen-2-yl)-amide, 4, (0.040 g, 0.11 mmol), 37% aq. formaldehyde (0.052 mL, 0.64 mmol) and NaBH(OAc)$_3$ (0.091 g, 0.43 mmol) in DMF (2 mL) is stirred at room temperature for 1 hour. The product is then isolated from the reaction matrix by reversed phase prep-HPLC using CH$_3$CN—H$_2$O (0.1% TFA) as eluent to afford 18 mg (45% yield) of the desired product as a foaming solid. $^1$H NMR (300 MHz, CD$_3$OD) δ 7.89 (d, J=8.4 Hz, 2H), 7.70 (m, 4H), 7.31 (m, 5H), 4.33 (m, 1H), 4.13 (s, 2H), 2.81-3.20 (m, 4H), 2.78 (s, 6H), 2.15 (br, 1H), 1.88 (m, 1H); $^{13}$C NMR (75 MHz, CD3OD) δ 166.3, 163.1 (d, J=243.6 Hz), 142.6, 137.1, 136.7, 136.5, 134.4, 133.6, 130.6, 129.7, 129.6, 129.5 (d, J=8.6 Hz), 128.6, 127.0, 117.1 (d, J=20.6 Hz), 65.8, 48.8, 46.7, 35.6, 29.4, 28.7; $^{19}$F NMR (282 MHz, CD$_3$OD) δ 46.0; LRMS: 403.6 (M+H); HRMS: calcd for C$_{26}$H$_{28}$FN$_2$O: 403.2186 (M+H), found: 403.2116.

For compounds which comprise the first aspect of Category 1 wherein R$^1$ and R$^2$ are alkyl units other than methyl, the artisan can substitute other aldehydes for formaldehyde in Scheme II, preparation of compound 5, inter alia, acetaldehyde, or ketones, for example, acetone in the case of isopropyl units. It may however, be necessary to adjust the stoichiometry of reagents, especially in the case on non-equivalent R$^1$ and R$^2$ units, and to adjust the conditions of the reductive amination in general.

The following are non-limiting examples of the first aspect of Category I according to the present invention.

4'-Fluoro-biphenyl-4-carboxylic acid [6-(isopropylamino-methyl)-1,2,3,4-tetrahydro-naphthalen-2-yl]-amide $^1$H NMR (300 MHz, CD3OD) δ 7.83 (d, J=8.4 Hz, 2H), 7.15 (m, 4H), 7.10 (m, 5H), 4.20 (m, 1H), 4.03 (s, 2H), 3.31 (m, 1H), 3.12 (dd, J=4.8, 16.3 Hz, 1H), 2.89 (dd, J=4.3, 8.3 Hz, 2H), 2.78 (dd, J=10.5, 16.5 Hz, 1H), 2.11 (m, 1H), 1.78 (m, 1H), 1.17 (d, J=6.6 Hz, 6H); $^{13}$C NMR (75 MHz, CD$_3$OD) δ 166.3, 162.4 (d, J=88.0 Hz), 144.9, 138.4, 138.2, 137.9, 134.9 131.6, 131.5, 130.8, 130.5 (d, J=8.1 Hz), 129.5, 128.6, 128.3, 117.2 (d, J=21.7 Hz), 52.1, 49.9, 48.3, 36.5, 30.5, 29.9, 19.6; $^{19}$F NMR (282 MHz, CD$_3$OD) δ 46.0; LRMS: 417.1 (M+H); HRMS: calcd for C$_{27}$H$_{29}$FN$_2$O: 417.2342 (M+H), found: 417.2362.

4'-Fluoro-biphenyl-4-carboxylic acid (6-diethylaminomethyl-1,2,3,4-tetrahydro-naphthalen-(2S)-yl)-amide $^1$H NMR (300 MHz, CD$_3$OD) δ 7.95 (d, J=8.3 Hz, 2H), 7.74-7.64 (m, 4H), 7.31-7.12 (m, 5H), 4.43-4.22 (m, 1H), 4.39 (superimposed singlet, 2H), 3.28-3.13 (m, 5H), 3.06-3.02 (m, 2H), 2.92 (dd, J=16.3, 10.5 Hz, 1H), 2.37-2.16 (m, 1H), 2.04-1.84 (m, 1H), 1.37 (t, J=7.2 Hz, 6H). $^{13}$C NMR (75 MHz, CD$_3$OD) δ 169.7, 164.5 (d, J=246 Hz), 144.7, 138.7, 138.4, 137.7, 134.7, 132.5, 131.5, 130.2 (d, J=8 Hz, 2C), 129.5, 129.2 (2C), 128.7, 128.1 (2C), 116.9 (d, J=22 Hz, 2C), 57.2, 48.0 (2C), 47.9, 36.3, 30.2, 29.6, 9.2 (2C). $^{19}$F NMR (282 MHz, CD$_3$OD) δ 45.9. LRMS calcd for C$_{28}$H$_{32}$FN$_2$O (M+H): 431.25, found: 431.29.

4'-Trifluoromethyl-biphenyl-4-carboxylic acid (6-diethylaminomethyl-1,2,3,4-tetrahydro-naphthalen-(2S)-yl)-amide $^1$H NMR (300 MHz, CD$_3$OD) δ 7.98 (d, J=8.2 Hz, 2H), 7.87 (d, J=8.2 Hz, 2H), 7.82-7.76 (mult, 4H), 7.30-7.23 (mult, 3H), 4.32 (mult, 1H), 4.29 (s, 2H), 3.23-3.19 (mult, 5H), 3.05-3.01 (mult, 2H), 2.95-2.82 (series of mult, 2H), 2.29 (mult, 1H), 1.35 (t, J=7.2 Hz, 6H). $^{13}$C NMR (75 MHz, CD$_3$OD) δ 169.6, 145.2, 144.0, 138.7, 138.4, 135.7, 132.5, 131.5, 129.5, 129.4, 128.9, 128.7, 128.5, 127.0, 57.2, 48.0, 47.5, 36.3, 30.2, 29.6, 9.2. LRMS: 481.3 (M+H); HRMS: calcd for C$_{29}$H$_{32}$F$_3$N$_2$O: 481.2467 (M+H), found: 481.2459.

4'-Fluoro-biphenyl-4-carboxylic acid (6-dimethylaminomethyl-1,2,3,4-tetrahydro-naphthalen-(2S)-yl)-amide $^1$H NMR (300 MHz, CD$_3$OD) δ 7.96 (d, J=8.5 Hz, 2H), 7.78-7.65 (m, 4H), 7.33-7.13 (m, 5H), 4.39-4.29 (m, 1H), 4.27 (s, 2H), 3.25-3.19 (m, 1H), 3.10-3.01 (m, 2H), 2.96-2.73 (m, 1H), 2.87, (superimposed singlet, 6H), 2.28-2.15 (m, 1H), 2.05-1.84 (m, 1H). LRMS calcd for C$_{26}$H$_{28}$FN$_2$O (M+H): 403.22, found: 402.29.

4'-Trifluoromethyl-biphenyl-4-carboxylic acid (6-dimethylaminomethyl-1,2,3,4-tetrahydro-naphthalen-(2R)-yl)-amide $^1$H NMR (300 MHz, CD$_3$OD) δ 8.58 (d, J=7.7 Hz, 1H), 8.01 (d, J=8.4 Hz, 2H), 7.90 (d, J=8.1 Hz, 2H), 7.82 (t, J=8.1 Hz, 4H), 7.30 (d, J=10.2 Hz, 2H). 4.31-4.27 (mult, 1H), 4.27 (superimposed s, 2H), 3.33 (dd, J=3.3, 1.5 Hz, 1H), 3.06-3.02 (mult, 2H), 2.93-2.80 (mult, 1H), 2.86 (superimposed s, 6H), 2.25-2.22 (mult, 1H), 1.95-1.91 (mult, 1H); $^{13}$C NMR (75 MHz, CD$_3$OD) δ 169.5, 145.2, 144.0, 138.8, 138.4, 135.6, 132.5, 131.4, 129.4, 128.9, 128.5, 127.0, 126.3, 125.2, 124.7, 62.3, 48.0, 43.1, 36.3, 30.2, 29.6; Mass Spec.: LRMS: 453.24.

2',4'-Difluoro-biphenyl-4-carboxylic acid (6-diethylaminomethyl-1,2,3,4-tetrahydro-naphthalen-(2S)-yl)-amide $^1$H NMR (300 MHz, CD$_3$OD) δ 7.95 (d, J=8.1 Hz, 2H), 7.64 (d, J=8.1 Hz, 2H), 7.57 (m, 1H), 7.28 (d, J=8.4 Hz, 3H), 7.10 (t, J=8.7 Hz, 2H), 4.29 (s, 3H), 3.21 (m, 5H), 3.03 (m, 2H), 2.91 (m, 1H), 2.24 (m, 1H), 1.90 (m, 1H), 1.36 (t, J=7.2 Hz, 6H); $^{19}$F NMR (281 MHz, CD$_3$OD) δ 50.5 (t, J=6.1 Hz, 1F), 47.8 (d, J=8.9 Hz, 1F); $^{13}$C NMR (75 MHz, CD$_3$OD) δ 169.4, 162.2, 139.5, 138.5, 138.2, 135.0, 132.8, 132.3, 131.3, 130.0, 129.2, 128.6, 113.1, 112.7, 105.6, 105.3, 104.9, 57.0, 47.8, 42.1, 36.1, 30.0, 29.4, 9.0; HRMS: calcd for C$_{28}$H$_{31}$F$_2$N$_2$O: 449.2404, found: 449.2390 (M+H$^+$).

The second aspect of Category I relates to R$^a$-substituted-biphenyl-4-carboxylic acid (6-aminomethyl-1,2,3,4-tetrahydro-naphthalen-2-yl)-amides having the formula:

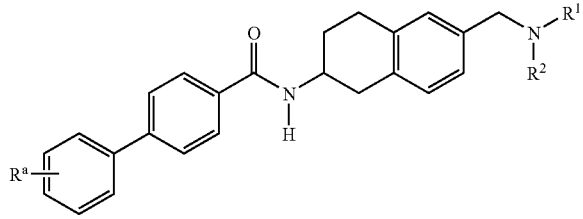

wherein $R^1$ and $R^2$ are taken together to form a heterocyclic ring containing from 3 to 8 atoms, and the $R^a$ substituted biphenyl units are defined herein in Table II.

TABLE II

| No. | $R^a$ containing unit | $R^1/R^2$ ring |
|---|---|---|
| 73 | 3'-fluoro-4-biphenyl | aziridin-1-yl |
| 74 | 3'-fluoro-4-biphenyl | pyrrolidin-1-yl |
| 75 | 3'-fluoro-4-biphenyl | piperidin-1-yl |
| 76 | 3'-fluoro-4-biphenyl | piperazin-1-yl |
| 77 | 3'-fluoro-4-biphenyl | morpholin-4-yl |
| 78 | 3'-fluoro-4-biphenyl | azepan-1-yl |
| 79 | 3'-chloro-4-biphenyl | aziridin-1-yl |
| 80 | 3'-chloro-4-biphenyl | pyrrolidin-1-yl |
| 81 | 3'-chloro-4-biphenyl | piperidin-1-yl |
| 82 | 3'-chloro-4-biphenyl | piperazin-1-yl |
| 83 | 3'-chloro-4-biphenyl | morpholin-4-yl |
| 84 | 3'-chloro-4-biphenyl | azepan-1-yl |
| 85 | 3'-trifluoromethyl-4-biphenyl | aziridin-1-yl |
| 86 | 3'-trifluoromethyl-4-biphenyl | pyrrolidin-1-yl |
| 87 | 3'-trifluoromethyl-4-biphenyl | piperidin-1-yl |
| 88 | 3'-trifluoromethyl-4-biphenyl | piperazin-1-yl |
| 89 | 3'-trifluoromethyl-4-biphenyl | morpholin-4-yl |
| 90 | 3'-trifluoromethyl-4-biphenyl | azepan-1-yl |
| 91 | 3'-cyano-4-biphenyl | aziridin-1-yl |
| 92 | 3'-cyano-4-biphenyl | pyrrolidin-1-yl |
| 93 | 3'-cyano-4-biphenyl | piperidin-1-yl |
| 94 | 3'-cyano-4-biphenyl | piperazin-1-yl |
| 95 | 3'-cyano-4-biphenyl | morpholin-4-yl |
| 96 | 3'-cyano-4-biphenyl | azepan-1-yl |
| 97 | 3'-nitro-4-biphenyl | aziridin-1-yl |
| 98 | 3'-nitro-4-biphenyl | pyrrolidin-1-yl |
| 99 | 3'-nitro-4-biphenyl | piperidin-1-yl |
| 100 | 3'-nitro-4-biphenyl | piperazin-1-yl |
| 101 | 3'-nitro-4-biphenyl | morpholin-4-yl |
| 102 | 3'-nitro-4-biphenyl | azepan-1-yl |
| 103 | 3'-methoxy-4-biphenyl | aziridin-1-yl |
| 104 | 3'-methoxy-4-biphenyl | pyrrolidin-1-yl |
| 105 | 3'-methoxy-4-biphenyl | piperidin-1-yl |
| 106 | 3'-methoxy-4-biphenyl | piperazin-1-yl |
| 107 | 3'-methoxy-4-biphenyl | morpholin-4-yl |
| 108 | 3'-methoxy-4-biphenyl | azepan-1-yl |
| 109 | 4'-fluoro-4-biphenyl | aziridin-1-yl |
| 110 | 4'-fluoro-4-biphenyl | pyrrolidin-1-yl |
| 111 | 4'-fluoro-4-biphenyl | piperidin-1-yl |
| 112 | 4'-fluoro-4-biphenyl | piperazin-1-yl |
| 113 | 4'-fluoro-4-biphenyl | morpholin-4-yl |
| 114 | 4'-fluoro-4-biphenyl | azepan-1-yl |
| 115 | 4'-chloro-4-biphenyl | aziridin-1-yl |
| 116 | 4'-chloro-4-biphenyl | pyrrolidin-1-yl |
| 117 | 4'-chloro-4-biphenyl | piperidin-1-yl |
| 118 | 4'-chloro-4-biphenyl | piperazin-1-yl |
| 119 | 4'-chloro-4-biphenyl | morpholin-4-yl |
| 120 | 4'-chloro-4-biphenyl | azepan-1-yl |
| 121 | 4'-trifluoromethyl-4-biphenyl | aziridin-1-yl |
| 122 | 4'-trifluoromethyl-4-biphenyl | pyrrolidin-1-yl |
| 123 | 4'-trifluoromethyl-4-biphenyl | piperidin-1-yl |
| 124 | 4'-trifluoromethyl-4-biphenyl | piperazin-1-yl |
| 125 | 4'-trifluoromethyl-4-biphenyl | morpholin-4-yl |
| 126 | 4'-trifluoromethyl-4-biphenyl | azepan-1-yl |
| 127 | 4'-cyano-4-biphenyl | aziridin-1-yl |
| 128 | 4'-cyano-4-biphenyl | pyrrolidin-1-yl |
| 129 | 4'-cyano-4-biphenyl | piperidin-1-yl |

TABLE II-continued

| No. | $R^a$ containing unit | $R^1/R^2$ ring |
|---|---|---|
| 130 | 4'-cyano-4-biphenyl | piperazin-1-yl |
| 131 | 4'-cyano-4-biphenyl | morpholin-4-yl |
| 132 | 4'-cyano-4-biphenyl | azepan-1-yl |
| 133 | 4'-nitro-4-biphenyl | aziridin-1-yl |
| 134 | 4'-nitro-4-biphenyl | pyrrolidin-1-yl |
| 135 | 4'-nitro-4-biphenyl | piperidin-1-yl |
| 136 | 4'-nitro-4-biphenyl | piperazin-1-yl |
| 137 | 4'-nitro-4-biphenyl | morpholin-4-yl |
| 138 | 4'-nitro-4-biphenyl | azepan-1-yl |
| 139 | 4'-methoxy-4-biphenyl | aziridin-1-yl |
| 140 | 4'-methoxy-4-biphenyl | pyrrolidin-1-yl |
| 141 | 4'-methoxy-4-biphenyl | piperidin-1-yl |
| 142 | 4'-methoxy-4-biphenyl | piperazin-1-yl |
| 143 | 4'-methoxy-4-biphenyl | morpholin-4-yl |
| 144 | 4'-methoxy-4-biphenyl | azepan-1-yl |

The compounds which comprise the second aspect of Category I of the present invention can be suitably prepared by the procedure outlined herein below in Scheme III beginning with intermediate 4.

Scheme III

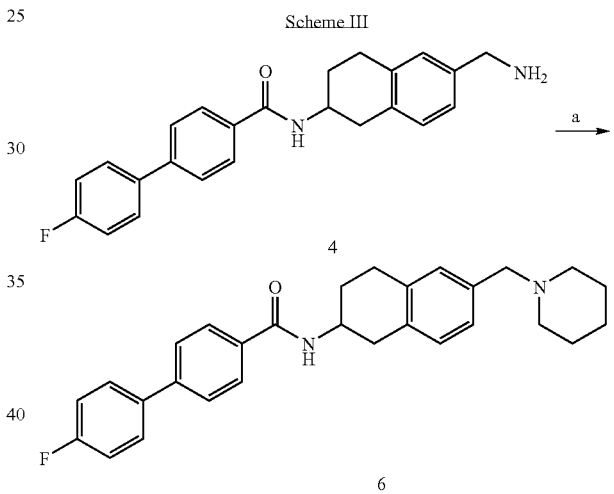

Reagents and conditions: (a) 1,5-dibromopentane, $K_2CO_3$, DMF; rt, 18 hr.

EXAMPLE 3

Preparation of 4'-fluoro-biphenyl-4-carboxylic acid (6-piperidin-1-ylmethyl-1,2,3,4-tetrahydro-naphthalen-2-yl)-amide A mixture of 4'-fluoro-biphenyl-4-carboxylic acid (6-aminomethyl-1,2,3,4-tetrahydro-naphthalen-2-yl)-amide, 4, (0.054 g, 0.14), dibromopentane (0.022 mL, 0.16 mmol) and $K_2CO_3$ (0.099 g, 0.72 mmol) in DMF (2 mL) is stirred at room temperature for 18 hours. The reaction solution is filtered and the filtrate concentrated in vacuo to leave a crude residue which is purified by reversed prep-HPLC using $CH_3CN-H_2O$ (0.1% TFA) to afforded 36 mg (57% yield) of the desired product as a foaming solid. $^1H$ NMR (300 MHz, $CD_3OD$) δ 7.94 (d, J=8.4 Hz, 2H), 7.72 (m, 4H), 7.25 (t, J=9.6 Hz, 5H), 4.33 (m, 1H), 4.24 (s, 2H), 3.44-3.56 (m, 3H), 3.16-3.24 (br, 1H), 2.84-3.07 (m, 4H), 2.20-2.35 (br, 1H), 1.67-2.02 (m, 6H), 1.54 (m, H1); $^{13}C$ NMR (75 MHz, CD$_3$OD) δ 168.4, 164.8, 143.4, 137.4, 137.0, 130.9, 131.5, 130.0, 128.9, 128.8, 128.5, 127.9, 126.8, 115.8, 115.5, 60.5, 52.7, 46.6, 35.0, 28.9, 28.3, 22.9, 21.6; $^{19}$F NMR (282 MHz, CD$_3$OD) δ 46.3; LRMS: 443.6 (M+H); HRMS: calcd for C$_{29}$H$_{32}$FN$_2$O: 443.2499 (M+H), found: 443.2506.

As it relates to compounds encompassed by the second aspect of Category I, wherein R$^1$ and R$^2$ can be taken together to form a heterocyclic ring having from 3 to 8 atoms, inter alia, pyrrolidine, piperazine, 1H-azepine, and morpholine, other reagents can be substituted for 1,5-dibromopentane, for example, 1,6-dibromohexane. However, the conditions may be necessarily adjusted by the formulator using practices standard and known to the skilled artisan.

Other non-limiting examples of compounds encompassed within Category I include:

4'-Fluoro-biphenyl-4-carboxylic acid (6-methylaminomethyl-1,2,3,4-tetrahydro-naphthalen-2-yl)-amide;

4'-Fluoro-biphenyl-4-carboxylic acid (6-ethylaminomethyl-1,2,3,4-tetrahydro-naphthalen-(2S)-yl)-amide;

4'-Fluoro-biphenyl-4-carboxylic acid (6-methylethylaminomethyl-1,2,3,4-tetrahydro-naphthalen-(2S)-yl)-amide;

4'-Fluoro-biphenyl-4-carboxylic acid (6-propylaminomethyl-1,2,3,4-tetrahydro-naphthalen-(2S)-yl)-amide;

4'-Fluoro-biphenyl-4-carboxylic acid (6-dipropylaminomethyl-1,2,3,4-tetrahydro-naphthalen-(2S)-yl)-amide;

4'-Fluoro-biphenyl-4-carboxylic acid [6-(diisopropylaminomethyl)-1,2,3,4-tetrahydro-naphthalen-2-yl]-amide;

4'-Fluoro-biphenyl-4-carboxylic acid [6-(methyl-isopropylaminomethyl)-1,2,3,4-tetrahydro-naphthalen-2-yl]-amide;

4'-Fluoro-biphenyl-4-carboxylic acid [6-(ethyl-isopropylaminomethyl)-1,2,3,4-tetrahydro-naphthalen-2-yl]-amide;

4'-Fluoro-biphenyl-4-carboxylic acid (6-piperazin-1-ylmethyl-1,2,3,4-tetrahydro-naphthalen-2-yl)-amide;

4'-Fluoro-biphenyl-4-carboxylic acid (6-aziridin-1-ylmethyl-1,2,3,4-tetrahydro-naphthalen-2-yl)-amide;

4'-Fluoro-biphenyl-4-carboxylic acid (6-pyrrolidin-1-ylmethyl-1,2,3,4-tetrahydro-naphthalen-2-yl)-amide;

4'-Fluoro-biphenyl-4-carboxylic acid (6-azepan-1-ylmethyl-1,2,3,4-tetrahydro-naphthalen-2-yl)-amide; and 4'-Fluoro-biphenyl-4-carboxylic acid (6-morpholin-4-ylmethyl-1,2,3,4-tetrahydro-naphthalen-2-yl)-amide.

Category II of the present invention relates to compounds with a core scaffold having the formula:

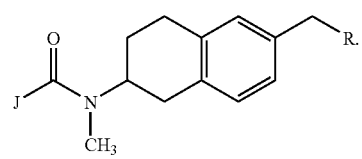

The first aspect of Category II relates to R$^a$-substituted-biphenyl-4-carboxylic acid [6-(R$^1$-alkyl-R$^2$-alkyl)-1,2,3,4-tetrahydro-naphthalen-2-yl]-methyl-amides having the formula:

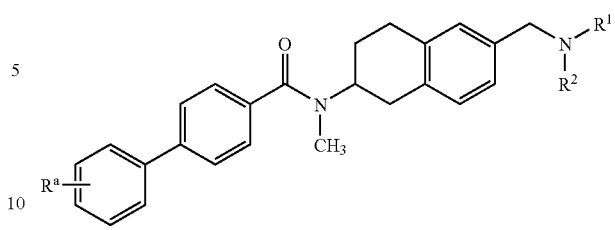

wherein R$^1$ and R$^2$ are each independently hydrogen or C$_1$-C$_3$ linear or branched alkyl, and the R$^a$ substituted biphenyl units are defined herein in Table III

| No. | R$^a$ containing unit | R$^1$ | R$^2$ |
|---|---|---|---|
| 145 | 4'-fluoro-4-biphenyl | —H | —H |
| 146 | 4'-fluoro-4-biphenyl | —H | —CH$_3$ |
| 147 | 4'-fluoro-4-biphenyl | —H | —CH$_2$CH$_3$ |
| 148 | 4'-fluoro-4-biphenyl | —H | —CH$_2$CH$_2$CH$_3$ |
| 149 | 4'-fluoro-4-biphenyl | —H | —CH(CH$_3$)$_2$ |
| 150 | 4'-fluoro-4-biphenyl | —CH$_3$ | —CH$_3$ |
| 151 | 4'-fluoro-4-biphenyl | —CH$_3$ | —CH$_2$CH$_3$ |
| 152 | 4'-fluoro-4-biphenyl | —CH$_3$ | —CH$_2$CH$_2$CH$_3$ |
| 153 | 4'-fluoro-4-biphenyl | —CH$_3$ | —CH(CH$_3$)$_2$ |
| 154 | 4'-fluoro-4-biphenyl | —CH$_2$CH$_3$ | —CH$_2$CH$_3$ |
| 155 | 4'-fluoro-4-biphenyl | —CH$_2$CH$_3$ | —CH$_2$CH$_2$CH$_3$ |
| 156 | 4'-fluoro-4-biphenyl | —CH$_2$CH$_3$ | —CH(CH$_3$)$_2$ |
| 157 | 2',4'-difluoro-4-biphenyl | —H | —H |
| 158 | 2',4'-difluoro-4-biphenyl | —H | —CH$_3$ |
| 159 | 2',4'-difluoro-4-biphenyl | —H | —CH$_2$CH$_3$ |
| 160 | 2',4'-difluoro-4-biphenyl | —H | —CH$_2$CH$_2$CH$_3$ |
| 161 | 2',4'-difluoro-4-biphenyl | —H | —CH(CH$_3$)$_2$ |
| 162 | 2',4'-difluoro-4-biphenyl | —CH$_3$ | —CH$_3$ |
| 163 | 2',4'-difluoro-4-biphenyl | —CH$_3$ | —CH$_2$CH$_3$ |
| 164 | 2',4'-difluoro-4-biphenyl | —CH$_3$ | —CH$_2$CH$_2$CH$_3$ |
| 165 | 2',4'-difluoro-4-biphenyl | —CH$_3$ | —CH(CH$_3$)$_2$ |
| 166 | 2',4'-difluoro-4-biphenyl | —CH$_2$CH$_3$ | —CH$_2$CH$_3$ |
| 167 | 2',4'-difluoro-4-biphenyl | —CH$_2$CH$_3$ | —CH$_2$CH$_2$CH$_3$ |
| 168 | 2',4'-difluoro-4-biphenyl | —CH$_2$CH$_3$ | —CH(CH$_3$)$_2$ |
| 169 | 4'-cyano-4-biphenyl | —H | —H |
| 170 | 4'-cyano-4-biphenyl | —H | —CH$_3$ |
| 171 | 4'-cyano-4-biphenyl | —H | —CH$_2$CH$_3$ |
| 172 | 4'-cyano-4-biphenyl | —H | —CH$_2$CH$_2$CH$_3$ |
| 173 | 4'-cyano-4-biphenyl | —H | —CH(CH$_3$)$_2$ |
| 174 | 4'-cyano-4-biphenyl | —CH$_3$ | —CH$_3$ |
| 175 | 4'-cyano-4-biphenyl | —CH$_3$ | —CH$_2$CH$_3$ |
| 176 | 4'-cyano-4-biphenyl | —CH$_3$ | —CH$_2$CH$_2$CH$_3$ |
| 177 | 4'-cyano-4-biphenyl | —CH$_3$ | —CH(CH$_3$)$_2$ |
| 178 | 4'-cyano-4-biphenyl | —CH$_2$CH$_3$ | —CH$_2$CH$_3$ |
| 179 | 4'-cyano-4-biphenyl | —CH$_2$CH$_3$ | —CH$_2$CH$_2$CH$_3$ |
| 180 | 4'-cyano-4-biphenyl | —CH$_2$CH$_3$ | —CH(CH$_3$)$_2$ |
| 181 | 4'-chloro-4-biphenyl | —H | —H |
| 182 | 4'-chloro-4-biphenyl | —H | —CH$_3$ |
| 1863 | 4'-chloro-4-biphenyl | —H | —CH$_2$CH$_3$ |
| 184 | 4'-chloro-4-biphenyl | —H | —CH$_2$CH$_2$CH$_3$ |
| 185 | 4'-chloro-4-biphenyl | —H | —CH(CH$_3$)$_2$ |
| 186 | 4'-chloro-4-biphenyl | —CH$_3$ | —CH$_3$ |
| 187 | 4'-chloro-4-biphenyl | —CH$_3$ | —CH$_2$CH$_3$ |
| 188 | 4'-chloro-4-biphenyl | —CH$_3$ | —CH$_2$CH$_2$CH$_3$ |
| 189 | 4'-chloro-4-biphenyl | —CH$_3$ | —CH(CH$_3$)$_2$ |
| 190 | 4'-chloro-4-biphenyl | —CH$_2$CH$_3$ | —CH$_2$CH$_3$ |
| 191 | 4'-chloro-4-biphenyl | —CH$_2$CH$_3$ | —CH$_2$CH$_2$CH$_3$ |
| 192 | 4'-chloro-4-biphenyl | —CH$_2$CH$_3$ | —CH(CH$_3$)$_2$ |
| 193 | 4'-methoxy-4-biphenyl | —H | —H |
| 194 | 4'-methoxy-4-biphenyl | —H | —CH$_3$ |
| 195 | 4'-methoxy-4-biphenyl | —H | —CH$_2$CH$_3$ |
| 196 | 4'-methoxy-4-biphenyl | —H | —CH$_2$CH$_2$CH$_3$ |
| 197 | 4'-methoxy-4-biphenyl | —H | —CH(CH$_3$)$_2$ |
| 198 | 4'-methoxy-4-biphenyl | —CH$_3$ | —CH$_3$ |
| 199 | 4'-methoxy-4-biphenyl | —CH$_3$ | —CH$_2$CH$_3$ |
| 200 | 4'-methoxy-4-biphenyl | —CH$_3$ | —CH$_2$CH$_2$CH$_3$ |
| 201 | 4'-methoxy-4-biphenyl | —CH$_3$ | —CH(CH$_3$)$_2$ |

-continued

| No. | R$^a$ containing unit | R$^1$ | R$^2$ |
|---|---|---|---|
| 202 | 4'-methoxy-4-biphenyl | —CH$_2$CH$_3$ | —CH$_2$CH$_3$ |
| 203 | 4'-methoxy-4-biphenyl | —CH$_2$CH$_3$ | —CH$_2$CH$_2$CH$_3$ |
| 204 | 4'-methoxy-4-biphenyl | —CH$_2$CH$_3$ | —CH(CH$_3$)$_2$ |
| 205 | 4'-trifluoromethyl-4-biphenyl | —H | —H |
| 206 | 4'-trifluoromethyl-4-biphenyl | —H | —CH$_3$ |
| 207 | 4'-trifluoromethyl-4-biphenyl | —H | —CH$_2$CH$_3$ |
| 208 | 4'-trifluoromethyl-4-biphenyl | —H | —CH$_2$CH$_2$CH$_3$ |
| 209 | 4'-trifluoromethyl-4-biphenyl | —H | —CH(CH$_3$)$_2$ |
| 210 | 4'-trifluoromethyl-4-biphenyl | —CH$_3$ | —CH$_3$ |
| 211 | 4'-trifluoromethyl-4-biphenyl | —CH$_3$ | —CH$_2$CH$_3$ |
| 212 | 4'-trifluoromethyl-4-biphenyl | —CH$_3$ | —CH$_2$CH$_2$CH$_3$ |
| 213 | 4'-trifluoromethyl-4-biphenyl | —CH$_3$ | —CH(CH$_3$)$_2$ |
| 214 | 4'-trifluoromethyl-4-biphenyl | —CH$_2$CH$_3$ | —CH$_2$CH$_3$ |
| 215 | 4'-trifluoromethyl-4-biphenyl | —CH$_2$CH$_3$ | —CH$_2$CH$_2$CH$_3$ |
| 216 | 4'-trifluoromethyl-4-biphenyl | —CH$_2$CH$_3$ | —CH(CH$_3$)$_2$ |

The compounds which comprise the first aspect of Category II can be prepared starting with compound 4 as outlined herein below in Scheme II.

Scheme IV

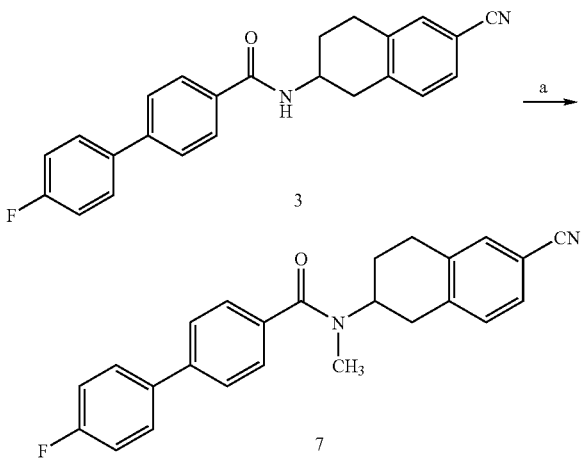

Reagents and conditions: (a) CH$_3$I, NaH, DMF; rt, 0.5 hr.

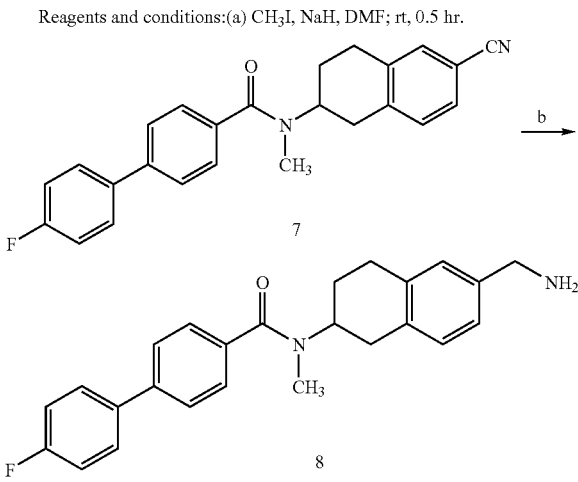

Reagents and conditions: (b) H$_2$, Raney Ni, NH$_4$OH, DMF; rt, 18 hr.

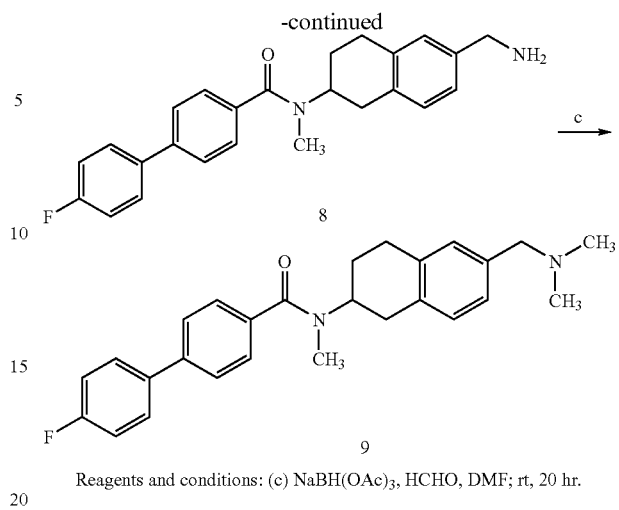

Reagents and conditions: (c) NaBH(OAc)$_3$, HCHO, DMF; rt, 20 hr.

EXAMPLE 4

4'-Fluoro-biphenyl-4-carboxylic acid (6-aminomethyl-1,2,3,4-tetrahydro-naphthalen-2-yl)-methyl-amide (9)

Preparation of 4'-fluoro-biphenyl-4-carboxylic acid (6-cyano-1,2,3,4-tetrahydro-naphthalen-2-yl)-methyl-amide (7)

To a solution of 4'-Fluoro-biphenyl-4-carboxylic acid (6-cyano-1,2,3,4-tetrahydro-naphthalen-2-yl)-amide, 3, (0.200 g, 0.541 mmol) in anhydrous DMF (4 mL) is added 60% NaH dispersed in mineral oil (32 mg, 1.5 eq.) and the resulting solution is stirred at room temperature for 30 min. Methyl iodide (0.101 mL, 3 eq.) is added to the solution and the reaction solution is stirred for another 30 min. A minimal amount of water is added to quench the reaction and the mixture is dried over anhydrous MgSO$_4$ then concentrated in vacuo to afford 0.201 g of the desired product which is used without further purification. LRMS: 385.22 (M+H).

Preparation of 4'-fluoro-biphenyl-4-carboxylic acid (6-aminomethyl-1,2,3,4-tetrahydro-naphthalen-2-yl)-methyl-amide (8)

A suspension of 4'-fluoro-biphenyl-4-carboxylic acid (6-cyano-1,2,3,4-tetrahydro-naphthalen-2-yl)-methyl-amide, 7, (0.200 g, 0.521 mmol), 28% NH$_4$OH (2 mL) and Raney Ni (0.2 g) in DMF (5 mL) is stirred vigorously at room temperature under 1 atm of H$_2$ for 18 hrs. The catalyst is removed by filtration and the filtrate is purified by directly loading to prep-HPLC column eluted with CH$_3$CN—H$_2$O (0.1% TFA) to afford 0.098 g of the desired product. $^1$H NMR (300 MHz, CD$_3$OD) δ 7.42-7.78 (m, 6H), 7.03-7.16 (m, 5H), 4.83 (m, 1H), 3.91-4.07 (m, 3H), 2.60-3.31 (m, 6H), 2.01-2.20 (m, 2H); $^{13}$C NMR (75 MHz, CD$_3$OD) δ 164.7, 161.4, 160.4, 141.7, 136.4, 135.5, 131.3, 130.0, 129.1, 128.8, 128.8, 127.0, 126.3, 115.7, 115.5, 56.0, 51.2, 42.9, 31.8, 29.0, 26.9; LRMS: 411.28 (M+Na), 388.27 (M+H), 372.25 (M+H–NH$_3$).

Preparation of 4'-fluoro-biphenyl-4-carboxylic acid (6-dimethylaminomethyl-1,2,3,4-tetrahydro-naphthalen-2-yl)-methyl-amide (9)

$^1$H NMR (300 MHz, DMF-D7) δ 7.94 (m, 4H), 7.76 (m, 2H), 7.32 (m, 2H), 7.24 (m, 3H), 4.43, (s, 6H), 3.91 (m, 1H), 3.49 (m, 3H), 3.01-3.37 (m, 4H), 2.24 (m, 2H); $^{19}$F NMR (282 MHz, DMF-D7) δ 46.60; LRMS: 439.25 (M+Na), 417.26 (M+H), 372.18 (M+H−HN(CH$_3$)$_2$) HRMS: calcd for C$_{27}$H$_{30}$FN$_2$O: 417.2342 (M+H), found: 417.2361.

The following are non-limiting examples of compounds according to the first aspect of Category II.

4'-Fluoro-biphenyl-4-carboxylic acid (6-dimethylaminomethyl-1,2,3,4-tetrahydro-naphthalen-(2S)-yl)-methyl-amide $^1$H NMR (300 MHz, DMSO-D6) δ 7.75 (m, 4H), 7.56 (m, 2H), 7.22 (m, 5H), 4.68 and 3.83 (2xs, 3H), 4.15 (m, 2H), 2.80-3.17 (m, 5H), 2.62-2.78 (m, 6H), 1.95-2.12 (m, 2H); $^{13}$C NMR (75 MHz, CD$_3$OD) δ 178.1, 164.5 (d, J=242 Hz), 143.3, 138.2, 138.5, 138.3, 138.0, 132.7, 131.7, 130.4, 130.3 (d, J=8 Hz), 129.8, 129.3, 128.6, 117.5 (d, J=22 Hz), 62.4, 57.4, 43.3, 34.0, 33.4, 32.8, 30.5; LRMS: 439.25 (M+Na), 417.26 (M+H), 372.18 (M+H−HNMe$_2$); HRMS: calcd for C$_{27}$H$_{30}$FN$_2$O: 417.2342 (M+H), found: 417.2361.

4'-Fluoro-biphenyl-4-carboxylic acid (6-diethylaminomethyl-1,2,3,4-tetrahydro-naphthalen-(2R)-yl)-methyl-amide $^1$H NMR (300 MHz, CD$_3$OD) δ 7.48-7.82 (m, 6H), 7.06-7.45 (m, 5H), 4.85, (m, 1H), 4.16-4.36 (m, 3H), 2.88-3.40 (m, 10H), 2.01-2.21 (m, 2H), 1.33 (br, 6H); $^{19}$F NMR (282 MHz, CD3OD) δ 46.3; LRMS: 445.32 (M+H), 372.19 (M+H−Et$_2$NH);

4'-Fluoro-biphenyl-4-carboxylic acid (6-diethylaminomethyl-1,2,3,4-tetrahydro-naphthalen-(2S)-yl)-methyl-amide $^1$H NMR (300 MHz, CD$_3$OD) δ 7.70 (s, 4H), 7.55 (s, 2H), 7.22 (m, 5H), 4.27 (m, 2H), 3.50 (m, 1H), 3.18-3.03 (m, 11H), 2.11 (s, 2H), 1.35 (s, 6H); $^{13}$C NMR (75 MHz, CD$_3$OD) δ 172.6, 163.1 (d, J=244.7 Hz), 141.7, 136.8, 136.4, 135.3, 131.2, 130.1, 129.3, 128.7 (d, J=7.9 Hz), 128.3, 127.5, 127.0, 126.9, 115.6 (d, J=21.9 Hz), 65.7, 55.8, 32.4, 31.9, 31.3, 28.9, 14.3, 7.9; $^{19}$F NMR (281 MHz, CD$_3$OD) δ 46. 1; HRMS: calcd for C$_{29}$H$_{34}$FN$_2$O: 445.2655, found: 445.2664 (M+H$^+$).

3',4'-Difluoro-biphenyl-4-carboxylic acid (6-dimethylaminomethyl-1,2,3,4-tetrahydro-naphthalen-(2S)-yl)-methyl amide.

$^1$H NMR (300 MHz, CD$_3$OD) δ 7.71 (s, 2H), 7.55-7.24 (m, 8H), 4.25 (m, 2H), 3.08-2.80 (m, 14H), 2.09 (m, 2H); $^{19}$F NMR (281 MHz, CD$_3$OD) δ 23.0 (s, 1F), 20.8 (s, 1F); $^{13}$C NMR (75 MHz, CD$_3$OD) δ 173.6, 153.4, 153.3, 149.8, 141.6, 138.7, 138.0, 137.5, 137.1, 132.3, 131.2, 129.3, 128.8, 128.2, 124.5, 118.8 (d, J=17.6 Hz), 116.9 (d, J=18.2 Hz), 61.9, 57.0, 52.2, 42.8, 33.6, 30.0, 28.4; HRMS: calcd for C$_{27}$H$_{29}$F$_2$N$_2$O: 435.2248, found: 435.2256 (M+H$^+$).

3'-Trifluoromethyl-biphenyl-4-carboxylic acid (6-dimethylaminomethyl-1,2,3,4-tetrahydro-naphthalen-(2S)-yl)-methyl amide.

$^1$H NMR (300 MHz, CDCl$_3$) δ 7.81-7.74 (m, 2H), 7.64-7.53 (m, 6H), 7.31-7.26 (m, 2H), 7.16-7.14 (m, 1H), 4.07 (s, 2H), 3.08-2.96 (m, 6H), 2.72 (s, 6H), 2.18-2.01 (series of m, 4H); $^{13}$C NMR (75 MHz, CDCl$_3$) δ 171.3, 140.9, 136.7, 136.2, 131.4 (2C), 131.0, 130.4 (2C), 129.4 (2C), 128.4 (2C), 127.4 (2C), 125.8, 124.4, 123.8, 122.2, 61.0, 54.9, 49.9, 42.1 (2C), 32.7, 29.1, 27.6; $^{19}$F NMR (282 MHz, CDCl$_3$) δ 100.1.

4'-Trifluoromethyl-biphenyl-4-carboxylic acid (6-dimethylaminomethyl-1,2,3,4-tetrahydro-naphthalen-(2S)-yl)-methyl amide $^1$H NMR (300 MHz, CDCl$_3$) δ 7.44-7.61 (m, 6H), 7.52-7.50 (m, 2H), 7.33-7.29 (m, 2H), 7.19-7.15 (m, 1H), 4.07-3.94 (m, 2H), 3.10-2.90 (m, 7H), 2.71 (s, 6H), 2.33-2.25 (m, 1H), 2.14-1.92 (m, 2H); $^{13}$C NMR (75 MHz, CDCl$_3$) δ171.3, 143.6, 140.9, 136.4, 131.4, 130.2, 129.9, 129.6, 128.4, 127.4, 126.1, 125.8, 125.7, 122.3, 61.0, 54.9, 50.1, 42.2, 31.5, 29.1, 27.5; $^{19}$F NMR (282 MHz, CDCl$_3$) δ 100.2; MS: found LRMS: 467.31.

4'-Trifluoromethyl-biphenyl-4-carboxylic acid (6-diethylaminomethyl-1,2,3,4-tetrahydro-naphthalen-(2S)-yl)-methyl amide $^1$H NMR (300 MHz, CD$_3$OD) δ 7.79 (s, 6H), 7.59 (s, 2H), 7.27 (m, 3H), 4.25 (d, J=18 Hz, 2H), 3.16-3.01 (m, 12H), 2.11 (s, 2H), 1.34 (s, 6H). $^{13}$C NMR (75 MHz, CD$_3$OD) δ 173.6, 145.0, 142.2, 138.6, 137.9, 137.6, 132.3, 131.3, 131.0, 130.5, 129.4, 128.7, 128.0, 127.5, 126.9, 56.9, 52.2, 47.7, 33.5, 32.9, 32.3, 29.9, 9.00; $^{19}$F NMR (280 MHz, CD$_3$OD) δ 99.0 (s, 3F); HRMS: Calcd. for C$_{30}$H$_{34}$N$_2$OF$_3$: 495.2623, found: 495.2615 (M+H$^+$).

The second aspect of Category II relates to R$^a$-substituted-biphenyl-4-carboxylic acid [6-(R$^1$-alkyl-R$^2$-alkyl)-1,2,3,4-tetrahydro-naphthalen-2-yl]-methyl-amides having the formula:

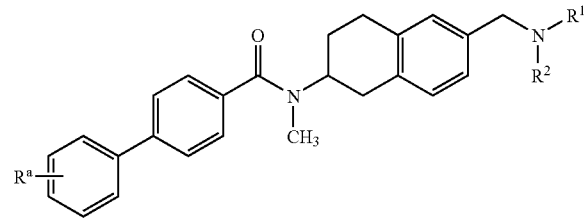

wherein R$^1$ and R$^2$ are taken together to form a heterocyclic ring containing from 3 to 8 atoms, and the R$^a$ substituted biphenyl units are defined herein in Table IV.

TABLE IV

| No. | R$^a$ containing unit | R$^1$/R$^2$ ring |
|---|---|---|
| 217 | 3'-fluoro-4-biphenyl | aziridin-1-yl |
| 218 | 3'-fluoro-4-biphenyl | pyrrolidin-1-yl |
| 219 | 3'-fluoro-4-biphenyl | piperidin-1-yl |
| 220 | 3'-fluoro-4-biphenyl | piperazin-1-yl |
| 221 | 3'-fluoro-4-biphenyl | morpholin-4-yl |

TABLE IV-continued

| No. | $R^a$ containing unit | $R^1/R^2$ ring |
|---|---|---|
| 222 | 3'-fluoro-4-biphenyl | azepan-1-yl |
| 223 | 3'-chloro-4-biphenyl | aziridin-1-yl |
| 224 | 3'-chloro-4-biphenyl | pyrrolidin-1-yl |
| 225 | 3'-chloro-4-biphenyl | piperidin-1-yl |
| 226 | 3'-chloro-4-biphenyl | piperazin-1-yl |
| 227 | 3'-chloro-4-biphenyl | morpholin-4-yl |
| 228 | 3'-chloro-4-biphenyl | azepan-1-yl |
| 229 | 3'-trifluoromethyl-4-biphenyl | aziridin-1-yl |
| 230 | 3'-trifluoromethyl-4-biphenyl | pyrrolidin-1-yl |
| 231 | 3'-trifluoromethyl-4-biphenyl | piperidin-1-yl |
| 232 | 3'-trifluoromethyl-4-biphenyl | piperazin-1-yl |
| 233 | 3'-trifluoromethyl-4-biphenyl | morpholin-4-yl |
| 234 | 3'-trifluoromethyl-4-biphenyl | azepan-1-yl |
| 235 | 3'-cyano-4-biphenyl | aziridin-1-yl |
| 236 | 3'-cyano-4-biphenyl | pyrrolidin-1-yl |
| 237 | 3'-cyano-4-biphenyl | piperidin-1-yl |
| 238 | 3'-cyano-4-biphenyl | piperazin-1-yl |
| 239 | 3'-cyano-4-biphenyl | morpholin-4-yl |
| 240 | 3'-cyano-4-biphenyl | azepan-1-yl |
| 241 | 3'-nitro-4-biphenyl | aziridin-1-yl |
| 242 | 3'-nitro-4-biphenyl | pyrrolidin-1-yl |
| 243 | 3'-nitro-4-biphenyl | piperidin-1-yl |
| 244 | 3'-nitro-4-biphenyl | piperazin-1-yl |
| 245 | 3'-nitro-4-biphenyl | morpholin-4-yl |
| 246 | 3'-nitro-4-biphenyl | azepan-1-yl |
| 247 | 3'-methoxy-4-biphenyl | aziridin-1-yl |
| 248 | 3'-methoxy-4-biphenyl | pyrrolidin-1-yl |
| 249 | 3'-methoxy-4-biphenyl | piperidin-1-yl |
| 250 | 3'-methoxy-4-biphenyl | piperazin-1-yl |
| 251 | 3'-methoxy-4-biphenyl | morpholin-4-yl |
| 252 | 3'-methoxy-4-biphenyl | azepan-1-yl |
| 253 | 4'-fluoro-4-biphenyl | aziridin-1-yl |
| 254 | 4'-fluoro-4-biphenyl | pyrrolidin-1-yl |
| 255 | 4'-fluoro-4-biphenyl | piperidin-1-yl |
| 256 | 4'-fluoro-4-biphenyl | piperazin-1-yl |
| 257 | 4'-fluoro-4-biphenyl | morpholin-4-yl |
| 258 | 4'-fluoro-4-biphenyl | azepan-1-yl |
| 259 | 4'-chloro-4-biphenyl | aziridin-1-yl |
| 260 | 4'-chloro-4-biphenyl | pyrrolidin-1-yl |
| 261 | 4'-chloro-4-biphenyl | piperidin-1-yl |
| 262 | 4'-chloro-4-biphenyl | piperazin-1-yl |
| 263 | 4'-chloro-4-biphenyl | morpholin-4-yl |
| 264 | 4'-chloro-4-biphenyl | azepan-1-yl |
| 265 | 4'-trifluoromethyl-4-biphenyl | aziridin-1-yl |
| 266 | 4'-trifluoromethyl-4-biphenyl | pyrrolidin-1-yl |
| 267 | 4'-trifluoromethyl-4-biphenyl | piperidin-1-yl |
| 268 | 4'-trifluoromethyl-4-biphenyl | piperazin-1-yl |
| 269 | 4'-trifluoromethyl-4-biphenyl | morpholin-4-yl |
| 270 | 4'-trifluoromethyl-4-biphenyl | azepan-1-yl |
| 271 | 4'-cyano-4-biphenyl | aziridin-1-yl |
| 272 | 4'-cyano-4-biphenyl | pyrrolidin-1-yl |
| 273 | 4'-cyano-4-biphenyl | piperidin-1-yl |
| 274 | 4'-cyano-4-biphenyl | piperazin-1-yl |
| 275 | 4'-cyano-4-biphenyl | morpholin-4-yl |
| 276 | 4'-cyano-4-biphenyl | azepan-1-yl |
| 277 | 4'-nitro-4-biphenyl | aziridin-1-yl |
| 278 | 4'-nitro-4-biphenyl | pyrrolidin-1-yl |
| 279 | 4'-nitro-4-biphenyl | piperidin-1-yl |
| 280 | 4'-nitro-4-biphenyl | piperazin-1-yl |
| 281 | 4'-nitro-4-biphenyl | morpholin-4-yl |
| 282 | 4'-nitro-4-biphenyl | azepan-1-yl |
| 283 | 4'-methoxy-4-biphenyl | aziridin-1-yl |
| 284 | 4'-methoxy-4-biphenyl | pyrrolidin-1-yl |
| 285 | 4'-methoxy-4-biphenyl | piperidin-1-yl |
| 286 | 4'-methoxy-4-biphenyl | piperazin-1-yl |
| 287 | 4'-methoxy-4-biphenyl | morpholin-4-yl |
| 288 | 4'-methoxy-4-biphenyl | azepan-1-yl |

The compounds which comprise the second aspect of Category II can be prepared from Intermediate 8 using the conditions found in step a of Scheme III herein above. The following is a non-limiting example of a compound according to the second aspect of Category II.

4'-Fluoro-biphenyl-4-carboxylic acid (6-piperidin-1-ylmethyl-1,2,3,4-tetrahydro-naphthalen-(2S)-yl)-methyl amide $^1$H NMR (300 MHz, CD$_3$OD) δ 7.60 (m, 6H), 7.20 (m, 5H), 4.17 (m, 2H), 3.40 (s, 2H), 2.99 (bs, 10H), 2.08 (s, 2H), 1.84 (m, 5H), 1.47 (s, 1H); $^{19}$F NMR (281 MHz, CD$_3$OD) δ 46.1 (1F); $^{13}$C NMR (75 MHz, CD$_3$OD) δ 172.6, 163.0 (d, J=240.0 Hz), 141.6, 136.8, 136.7, 136.3, 135.4, 131.4, 130.0, 128.8 (d, J=8.0 Hz), 128.5, 127.5, 127.0, 126.9, 115.5 (d, J=21.9 Hz), 60.3, 55.9, 55.8, 52.6, 51.1, 48.7, 28.9, 22.8, 21.5; HRMS: calcd for C$_{30}$H$_{34}$FN$_2$O: 457.2655, found: 457.2637 (M+H$^+$).

Further non-limiting examples of compounds according to Category II of the present invention include:

4'-Fluoro-biphenyl-4-carboxylic acid (6-methylaminomethyl-1,2,3,4-tetrahydro-naphthalen-2-yl)-methyl-amide;

4'-Fluoro-biphenyl-4-carboxylic acid (6-ethylaminomethyl-1,2,3,4-tetrahydro-naphthalen-2-yl)-methyl-amide;

4'-Fluoro-biphenyl-4-carboxylic acid (6-methyl-ethylaminomethyl-1,2,3,4-tetrahydro-naphthalen-2-yl)-methyl-amide;

4'-Fluoro-biphenyl-4-carboxylic acid (6-propylaminomethyl-1,2,3,4-tetrahydro-naphthalen-2-yl)-methyl-amide;

4'-Fluoro-biphenyl-4-carboxylic acid (6-dipropylaminomethyl-1,2,3,4-tetrahydro-naphthalen-2-yl)-methyl-amide;

4'-Fluoro-biphenyl-4-carboxylic acid (6-isopropylaminomethyl-1,2,3,4-tetrahydro-naphthalen-2-yl)-methyl-amide;

4'-Fluoro-biphenyl-4-carboxylic acid (6-diisopropylaminomethyl-1,2,3,4-tetrahydro-naphthalen-2-yl)-methyl-amide;

4'-Fluoro-biphenyl-4-carboxylic acid (6-piperazin-1-ylmethyl-1,2,3,4-tetrahydro-naphthalen-(2S)-yl)-methyl amide;

4'-Fluoro-biphenyl-4-carboxylic acid (6-pyrrolidin-1-ylmethyl-1,2,3,4-tetrahydro-naphthalen-(2S)-yl)-methyl amide;

4'-Fluoro-biphenyl-4-carboxylic acid (6-aziridin-1-ylmethyl-1,2,3,4-tetrahydro-naphthalen-(2S)-yl)-methyl amide;

4'-Fluoro-biphenyl-4-carboxylic acid (6-azepan-1-ylmethyl-1,2,3,4-tetrahydro-naphthalen-(2S)-yl)-methyl amide; and 4'-Fluoro-biphenyl-4-carboxylic acid (6-morpholin-4-ylmethyl-1,2,3,4-tetrahydro-naphthalen-(2S)-yl)-methyl amide.

The analogs (compounds) of the present invention are arranged in several categories to assist the formulator in applying a rational synthetic strategy for the preparation of analogs which are not expressly exampled herein. The arrangement into categories does not imply increased or decreased efficacy for any of the compositions of matter described herein.

Compounds listed and described herein above have been found in many instances to exhibit activities (IC$_{50}$ in the cell based assay described herein below or ones which are referenced herein) at a level below 1 micromolar (μM).

Each of the disease states or conditions which the formulator desires to treat may require differing levels or amounts of the compounds described herein to obtain a therapeutic level. The formulator can determine this amount by any of the common testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select if necessary one salt form of the present analogs over another since the compounds themselves are the active species which mitigate the disease processes described herein.

Pro-Drug Forms

Related to this aspect are the various precursor or "pro-drug" forms of the analogs of the present invention. It may be desirable to formulate the compounds of the present invention as a chemical species which itself is not an antagonist against melanin concentrating hormone as described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

The pro-drugs of the present invention can have any form suitable to the formulator, for example, esters are common pro-drug forms. In the present case, however, the pro-drug may necessarily exist in a form wherein a covalent bond is cleaved by the action of an enzyme present at the target situs. For example, a C—C covalent bond may be selectively cleaved by one or more enzymes at said target situs and, therefore, a pro-drug in a form other than an easily hydrolysable precursor, inter alia, esters, amides, and the like, may be utilized.

For the purposes of the present invention the term "therapeutically suitable pro-drug" is defined herein as "a melanin concentrating hormone antagonist modified in such a way as to be transformed in vivo to the therapeutically active from, whether by way of a single or by multiple biological transformations, when in contact with the tissues of humans or mammals to which the pro-drug has been administered, and without undue toxicity, irritation, or allergic response, and achieving the intended therapeutic outcome."

A detailed description of pro-drug derivatives can be found in the following included herein by reference:
a) *Design of Prodrugs*, edited by H. Bundgaard, (Elsevier, 1985);
b) *Methods in Enzymology*, 42, 309-396, edited by K. Widder et al. (Academic Press, 1985);
c) *A Textbook of Drug Design and Development*, edited by Krogsgaard-Larsen and H. Bundgaard, Chapter 5, "Design and Application of Prodrugs." By H. Bundgaard, 113-191 (1991);
d) *Advanced Drug Delivery Reviews*, H. Bundgaard, 8, 1-38 (1992);
e) *Chem Pharm Bull*, N. Kakeya et al., 32, 692 (1984).

Formulations

The present invention also relates to compositions or formulations which comprise the melanin concentrating hormone antagonists according to the present invention. In general, the second aspect of the present invention relates to pharmaceutical compositions said compositions comprising:
  A) an effective amount of one or more of the melanin concentrating hormone antagonists described herein; and
  B) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the antagonists against melanin concentrating hormone activity. In general, these precursor-comprising compositions of the present invention comprise:
  A) an effective amount of one or more melanin concentrating hormone antagonists as described herein above; and
  B) one or more pharmaceutically acceptable excipients.

Method of Use

Many human and mammalian disorders result from too much body mass (obesity or other over weight condition). Controlling body mass is a first step in preventing, as well as effectively treating many diseases and disease states. Among the disorders which are modulated, attenuated, abated, or otherwise controlled by the compounds of the present invention which serve as antagonists of MCH activity, is human obesity. This condition has been shown to be directly related to a wide range of disorders. The compounds of the selective antagonists of the present invention are capable of treating diseases acting as antagonists of MCH activity with minimal, little, or no activity involving the $5-HT_{2c}$ receptor.

As antagonists of MCH action upon the MCH receptor, the compounds of the present invention are useful in treating disorders that are mediated by MCH through the MCH receptor. Additional disorders other than obesity and food intake related illnesses that are mediated by MCH through the MCH receptor are abnormalities in reproduction and sexual behavior (sexual dysfunction, penile erection), thyroid hormone secretion, diuresis and water/electrolyte homeostasis, sensory processing, memory, sleep and arousal, anxiety and depression, seizure and in treatment of neurodegeneration or psychiatric disorders. In addition, melanin concentrating hormone antagonists are also effective in treating disorders relating to cardiovascular function, inflammation, sepsis, cardiogenic and hypovolemic shock, muscle atrophy, nerve growth and repair, intrauterine fetal growth, and the like.

The compounds of the present invention have improved cellular potency and pharmacokinetic properties and this advantage is made use of by the fact the third aspect of the present invention as a whole, relates to a method for controlling obesity, and the subsequent weight management after weight loss. This is achieved by administering to a human or a higher mammal an effective amount of one or more of the compounds (analogs) as described herein. Non-limiting examples of diseases which are affected by an MCH antagonist activity are obesity and other body weight disorders, inter alia, anorexia and cachexia.

Melanin Concentrating Hormone (MCH) activity, to which the antagonists of the present invention are directed, and as discussed herein above, is not limited to modulation of food intake as effects on the hypothalamic-pituitary axis have been reported.[2]

2. *Critical Rev. in Neurobiol.*, Nahon, 8, 221-262 (1994).

The role of MCH in modulating a variety of biological functions, and, therefore, multiple disease states, was first established by Hawes et al. when they showed "that the MCH receptor couples to multiple G proteins to mediate several diverse intracellular signaling pathways."[3]

3. "The melanin-concentrating hormone receptor couples to multiple G proteins to activate diverse intracellular signaling pathways," Hawes, B. E. et al., *Endocrinology*, 141(12), 4524-32 (2000).

MCH is expressed in the lateral hypothalamic area, which also has an important role in the regulation of the autonomic nervous system, heart rate, and blood pressure. Astrand et al., showed that male mice lacking the rodent MCH receptor demonstrated a significantly increased heart rate with no significant difference in mean arterial pressure.[4]

4. "Mice lacking the Melanin Concentrating Hormone Receptor 1 demonstrate increased heart associated with altered autonomic activity," Astand, A. et al., *Am J Physiol Regul Integr Comp Physiol.* May 6, (2004).

Utilizing the melanin concentrating hormone antagonists of the present invention will therefore affect a variety of diseases, disease states, conditions, or syndromes resulting from body weight disorders, inter alia, insulin resistance, glucose intolerance, Type-2 diabetes mellitus, coronary artery disease, elevated blood pressure, hypertension, dyslipidaemia, cancer (e.g., endometrial, cervical, ovarian, breast, prostate, gallbladder, colon), menstrual irregularities, hirsutism, infertility, gallbladder disease, restrictive lung disease, sleep apnea, gout, osteoarthritis, and thromboembolic disease.

Although the melanin concentrating hormone antagonists of the present invention are discrete chemical entities, the method of delivery or the method of use may be coupled with other suitable drug delivery systems. For example, a drug delivery technique useful for the compounds of the present invention is the conjugation of the compound to an active molecule capable of being transported through a biological barrier.[5] A specific example constitutes the coupling of the compound of the invention to fragments of insulin to achieve transport across the blood brain barrier.[6]

5. Zlokovic, B. V., *Pharmaceutical Research*, Vol. 12, pp. 1395-1406 (1995).
6. Fukuta, M., et al. *Pharmaceutical Res.*, Vol. 11, pp. 1681-1688 (1994).

For general reviews of technologies for drug delivery suitable for the compounds of the invention see:

Zlokovic, B. V., *Pharmaceutical Res.*, Vol. 12, pp. 1395-1406 (1995) and Pardridge, W M, *Pharmacol. Toxicol.*, Vol. 71, pp. 3-10 (1992).

The compounds of the present invention which are selective antagonists at the MCH-1R receptor over the 5-HT$_{2c}$ receptor are suitable for use the following:

A method for controlling the body weight of humans and higher mammals, said method comprising administering to a human or higher mammal an effective amount of one or more selective antagonists of the present invention, including all enantiomeric and diasteriomeric forms and pharmaceutically acceptable salts thereof.

A method for controlling weight loss in humans and higher mammals, said method comprising administering to a human or higher mammal an effective amount of one or more selective antagonists of the present invention, including all enantiomeric and diasteriomeric forms and pharmaceutically acceptable salts thereof.

A method for controlling in humans one or more diseases, disease states, conditions, or syndromes relating to behavior, said diseases, disease states, conditions, or syndromes are chosen from memory impairment (including learning), cardiovascular function, inflammation, sepsis, cardiogenic and hypovolemic shock, sexual dysfunction, penile erection, muscle atrophy, nerve growth and repair, and intrauterine fetal growth comprising administering an effective amount of one or more selective antagonists of the present invention, including all enantiomeric and diasteriomeric forms and pharmaceutically acceptable salts thereof.

A method for controlling in humans one or more diseases, disease states, conditions, or syndromes resulting from body weight disorders, said diseases, disease states, conditions, or syndromes are chosen from insulin resistance, glucose intolerance, Type-2 diabetes mellitus, coronary artery disease, elevated blood pressure, hypertension, dyslipidaemia, endometrial cancer, cervical cancer, ovarian cancer, breast cancer, prostate cancer, gallbladder cancer, colon cancer, menstrual irregularities, hirsutism, infertility, gallbladder disease, restrictive lung disease, sleep apnea, gout, osteoarthritis, and thromboembolic disease, said method comprising administering to a human an effective amount of one or more selective antagonist of the present invention, including all enantiomeric and diasteriomeric forms and pharmaceutically acceptable salts thereof.

Procedures

Binding and Functional Assays for Melanin Concentrating Hormone (MCH)

In vitro binding and function assays are performed on membranes derived from cells or tissues expressing endogenous MCH1R. Competition binding assays are performed to identify high affinity compounds. Briefly, either radiolabeled or europium labeled MCH with varying concentrations of competitor compound are incubated with membranes expressing the receptor. Rat brain membrane or cell lines, including but not limited to human Kelly neuroblastoma cells, A-431 epidermoid cells, and rat PC-12 cells are known to express endogenous MCH1R and are used in the assay. Binding is allowed to proceed until equilibrium is reached then bound labeled MCH is separated from free MCH by capturing membranes onto a filter. The filters are washed to remove loosely associated MCH and labeled MCH is quantified. Data is analyzed and IC$_{50}$ and K$_i$ are calculated to determine compound affinity.

MCH function assays are performed in an analogous manner to the binding assay. Competition assays are performed with a single concentration of MCH and varying concentrations of compound. Function is assayed using GTP binding or a functional response (e.g. Calcium uptake, MAP/ERK activation) because the MCH1R is a G-protein coupled receptor that couples the G$_{i/o}$ and G$_q$ proteins and has been shown to elicit these cellular functional responses. The assay can be performed on the same membranes as used for the binding assays. There are readily available kits for measuring GTP binding to membranes (e.g. Perkin Elmer Life Sciences). Data is analyzed and IC$_{50}$ values are generated to determine whether the compound is an agonist or antagonist.

Binding Assays for Serotonin Receptor, 5-HT$_{2c}$ Receptor

MCH antagonist compounds are evaluated for binding to the serotonin 5-HT$_{2c}$ receptor to determine receptor selectivity. Binding activity is assessed using a competitive assay with ³H-mesulergine (Perkin Elmer), a 5-HT$_{2c}$ selective ligand, on membranes containing the 5-HT$_{2c}$ receptor. Briefly, 1 nM ³H-mesulergine and varying concentrations of the compound are incubated with 5-HT$_{2c}$ receptor membranes, following an incubation period, the membranes are washed and ³H-mesulergine bound to membranes is measured in a liquid scintillation counter. The amount of bound ³H-mesulergine at the varying concentration of competitor compound is used to derive the affinity (K$_i$) of the compound for the 5-HT$_{2c}$ receptor. 5-HT$_{2c}$ receptor containing membranes are readily available from several companies including Perkin-Elmer and Euroscreen.

The following table shows IC$_{50}$ (nM) binding data for selected compounds at both the MCH1R and 5-HT$_{2c}$ receptors.

TABLE V

| Compound | MCH1R | 5-HT2C |
| --- | --- | --- |
| 4'-Fluoro-biphenyl-4-carboxylic acid (6-dimethylaminomethyl-1,2,3,4-tetrahydro-naphthalen-(2S)-yl)-methyl-amide | 60 | >100,000 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, including all enantiomeric and diastereomeric forms and pharmaceutically acceptable salts thereof, said compound having the formula:

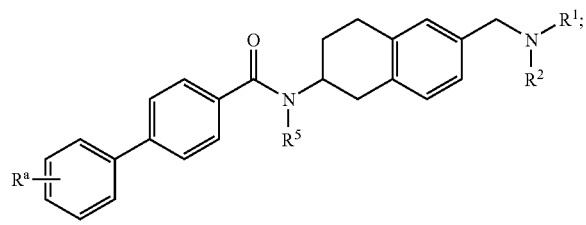

wherein:
A) R$^a$ is one or more substitutions for hydrogen, said substitutions independently chosen from:
  i) fluoro;
  ii) chloro;
  iii) cyano;
  iv) trifluoromethyl;
  v) nitro; and
  vi) methyl;
B) R$^1$ and R$^2$ are each independently selected from the group consisting of:
  i) hydrogen;
  ii) substituted or unsubstituted C$_1$-C$_8$ linear, branched or cyclic alkyl; or iii) R$^1$ and R$^2$ can be taken together to form a substituted or unsubstituted heterocyclic ring having from 3 to 8 ring atoms;
said substitutions chosen from:
  a) —OH;
  b) —F;
  c) —CF$_3$;
  d) —C(O)CH$_3$;
  e) —C(O)NH$_2$;
  f) —C(O)NHCH$_3$;
  g) —C(O)N(CH$_3$)$_2$;
  h) —CH$_2$C(O)NHCH$_3$;
  i) —CH$_2$C(O)N(CH$_3$)$_2$;
  j) —CH$_2$OCH$_3$;
  k) —CH$_2$CO$_2$H;
  l) —CH$_2$CO$_2$CH$_3$;
  m) —CH$_2$CO$_2$CH$_2$CH$_3$; and
  n) —NH$_2$CO$_2$CH$_3$; and
C) R$^5$ is hydrogen or methyl.

2. A compound according to claim 1 wherein the moiety

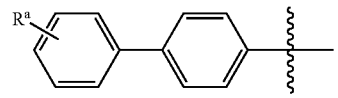

is chosen from biphenyl, 3'-fluoro-biphenyl, 3'-chloro-biphenyl, 3'-nitro-biphenyl, 3'-cyano-biphenyl, 3'-hydroxy-biphenyl, 3'-methoxy-biphenyl, 3'-trifluoromethyl-biphenyl, 3'-methyl-biphenyl, 4'-fluoro-biphenyl, 4'-chloro-biphenyl, 4'-nitro-biphenyl, 4'-cyano-biphenyl, 4'-hydroxy-biphenyl, 4'-methoxy-biphenyl, 4'-trifluoromethyl-biphenyl, 4'-methyl-biphenyl, 2',4'-difluoro-biphenyl, 3',4'-difluoro-biphenyl, 2',4'-dichloro-biphenyl, 3',4'-dichloro-biphenyl, 3'-fluoro-4'-chloro-biphenyl, and 3'-chloro-4'-fluoro-biphenyl.

3. A compound according to claim 1 wherein the moiety

is chosen from:
  i) —NH$_2$;
  ii) —NH(CH$_3$);
  iii) —NH(CH$_2$CH$_3$);
  iv) N(CH$_3$)$_2$;
  v) —N(CH$_3$)(CH$_2$CH$_3$);
  vi) N(CH$_2$CH$_3$)$_2$;
  vii) NH[CH(CH$_3$)$_2$];
  viii) N[CH(CH$_3$)$_2$]$_2$;
  ix) —NH[CH$_2$CH(OH)CH$_3$];
  x) —NCH$_3$[CH$_2$CH(OH)CH$_3$];
  xi) —NCH$_3$[CH$_2$CH$_2$OH];
  xii) —N[CH(CH$_3$)$_2$][CH$_2$CH$_2$OH];
  xiii) NCH$_3$(C$_6$H$_{11}$); and
  xiv) N[CH(CH$_3$)$_2$](C$_6$H$_{11}$).

4. A compound according to claim 1 wherein the moiety

is chosen from:
i) azetidin-1-yl;
ii) pyrrolidin-1-yl;
iii) 2-(dimethylamidomethyl)pyrrolidin-1-yl;
iv) 2-(methoxymethyl)pyrrolidin-1-yl;
v) 3-hydroxypyrrolidin-1-yl;
vi) 3-(carboxymethyl)pyrrolidin-1-yl; and
vii) 3-(ethylcarboxymethyl)pyrrolidin-1-yl.

5. A compound according to claim 1 wherein the moiety

is chosen from:
i) piperidin-1-yl;
ii) 4-methylpiperidin-1-yl;
iii) 3-hydroxypiperidin-1-yl;
iv) 4-hydroxypiperidin-1-yl;
v) 4,4-difluoropiperidin-1-yl;
vi) 4-trifluoromethylpiperidin-1-yl;
vii) 4-trifluoromethyl-4-hydroxypiperidin-1-yl;
viii) 4-methanesulfonylpiperidin-1-yl;
ix) piperazin-1-yl;
x) 4-methylpiperazin-1-yl;
xi) 4-acetylpiperazin-1-yl;
xii) 4-(acetamido)piperazin-1-yl;
xiii) 4-(methylcarboxy)piperazin-1-yl;
xiv) 7-azabicyclo[2.2.1]hept-7-yl;
xv) 2-oxa-5-azabicyclo[2.2.1]hept-5-yl;
xvi) 5-acetyl-2,5-diazabicyclo[2.2.1]hept-2-yl;
xvii) 1-oxo-2,8-diazaspiro[4.5]dec-8-yl; and
xviii) morpholin-4-yl.

6. A compound according to claim 1 wherein $R^5$ is methyl.

7. A compound having the formula:

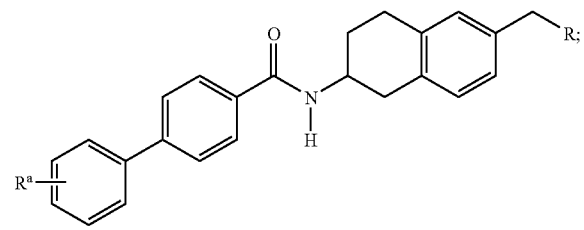

wherein:
A) R is an amino unit having the formula:

B) $R^1$ and $R^2$ are each independently selected from the group consisting of:
i) hydrogen;
ii) substituted or unsubstituted $C_1$-$C_8$ linear, branched or cyclic alkyl; or
iii) $R^1$ and $R^2$ can be taken together to form a substituted or unsubstituted heterocyclic ring having from 3 to 8 ring atoms;
said substitutions chosen from:
a) —OH;
b) halogen;
c) —$CF_3$;
d) —$C(O)CH_3$;
e) —$C(O)NH_2$;
f) —$C(O)NHCH_3$;
g) —$C(O)N(CH_3)_2$;
h) —$CH_2C(O)NHCH_3$;
i) —$CH_2C(O)N(CH_3)_2$;
j) —$CH_2OCH_3$;
k) —$CH_2CO_2H$;
l) —$CH_2CO_2CH_3$;
m) —$CH_2CO_2CH_2CH_3$; and
n) —$NH_2CO_2CH_3$; and C) $R^a$ is one or more substitutions for hydrogen, said substitutions independently chosen from:
i) fluoro;
ii) chloro;
iii) cyano;
iv) trifluoromethyl;
v) nitro; and
vi) methyl.

8. A compound having the formula:

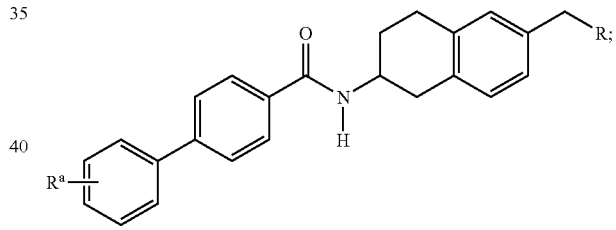

wherein:
A) R is an amino unit having the formula:

B) $R^1$ and $R^2$ are each independently selected from the group consisting of:
i) hydrogen;
ii) substituted or unsubstituted $C_1$-$C_8$ linear, branched or cyclic alkyl; or
iii) $R^1$ and $R^2$ can be taken together to form a substituted or unsubstituted heterocyclic ring having from 3 to 8 ring atoms;
said substitutions chosen from:
a) —OH;
b) halogen;
c) —$CF_3$;
d) —$C(O)CH_3$;

e) —C(O)NH$_2$;
f) —C(O)NHCH$_3$;
g) —C(O)N(CH$_3$)$_2$;
h) —CH$_2$C(O)NHCH$_3$;
i) —CH$_2$C(O)N(CH$_3$)$_2$;
j) —CH$_2$OCH$_3$;
k) —CH$_2$CO$_2$H;
l) —CH$_2$CO$_2$CH$_3$;
m) —CH$_2$CO$_2$CH$_2$CH$_3$; and
n) —NH$_2$CO$_2$CH$_3$; and C) R$^a$ is one or more substitutions for hydrogen, said substitutions independently chosen from:
   i) fluoro;
   ii) chloro;
   iii) cyano;
   iv) trifluoromethyl;
   v) nitro; and
   vi) methyl.

9. A compound chosen from:
4'-Fluorobiphenyl-4-carboxylic acid (6-aminomethyl-1,2,3,4-tetrahydro-naphthalen-2-yl)-amide;
4'-Fluorobiphenyl-4-carboxylic acid (6-methylaminomethyl-1,2,3,4-tetrahydro-naphthalen-2-yl)-amide;
4'-Fluorobiphenyl-4-carboxylic acid (6-dimethylaminomethyl-1,2,3,4-tetrahydro-naphthalen-2-yl)-amide;
4'-Fluorobiphenyl-4-carboxylic acid (6-ethylaminomethyl-1,2,3,4-tetrahydro-naphthalen-(2S)-yl)-amide;
4'-Fluorobiphenyl-4-carboxylic acid (6-diethylaminomethyl-1,2,3,4-tetrahydro-naphthalen-(2S)-yl)-amide;
4'-Fluorobiphenyl-4-carboxylic acid (6-methylethylaminomethyl-1,2,3,4-tetrahydro-naphthalen-(2S)-yl)-amide;
4'-Fluorobiphenyl-4-carboxylic acid (6-propylaminomethyl-1,2,3,4-tetrahydro-naphthalen-(2S)-yl)-amide;
4'-Fluorobiphenyl-4-carboxylic acid (6-dipropylaminomethyl-1,2,3,4-tetrahydro-naphthalen-(2S)-yl)-amide;
4'-Fluorobiphenyl-4-carboxylic acid [6-(isopropylamino-methyl)-1,2,3,4-tetrahydro-naphthalen-2-yl]-amide;
4'-Fluorobiphenyl-4-carboxylic acid [6-(diisopropylamino-methyl)-1,2,3,4-tetrahydro-naphthalen-2-yl]-amide;
4'-Fluorobiphenyl-4-carboxylic acid [6-(methyl-isopropylamino-methyl)-1,2,3,4-tetrahydro-naphthalen-2-yl]-amide;
4'-Fluorobiphenyl-4-carboxylic acid [6-(ethyl-isopropylamino-methyl)-1,2,3,4-tetrahydro-naphthalen-2-yl]-amide;
4'-Trifluoromethyl-biphenyl-4-carboxylic acid (6-diethylaminomethyl-1,2,3,4-tetrahydro-naphthalen-(2S)-yl)-amide;
4'-Trifluoromethyl-biphenyl-4-carboxylic acid (6-dimethylaminomethyl-1,2,3,4-tetrahydro-naphthalen-(2R)-yl)-amide;
2',4'-DiFluorobiphenyl-4-carboxylic acid (6-diethylaminomethyl-1,2,3,4-tetrahydro-naphthalen-(2S)-yl)-amide;
4'-Fluorobiphenyl-4-carboxylic acid (6-pyrrolidin-1-ylmethyl-1,2,3,4-tetrahydro-naphthalen-2-yl)-amide;
4'-Fluorobiphenyl-4-carboxylic acid (6-piperidin-1-ylmethyl-1,2,3,4-tetrahydro-naphthalen-2-yl)-amide;
4'-Fluorobiphenyl-4-carboxylic acid (6-piperazin-1-ylmethyl-1,2,3,4-tetrahydro-naphthalen-2-yl)-amide;
4'-Fluorobiphenyl-4-carboxylic acid (6-aziridin-1-ylmethyl-1,2,3,4-tetrahydro-naphthalen-2-yl)-amide;
4'-Fluorobiphenyl-4-carboxylic acid (6-azepan-1-ylmethyl-1,2,3,4-tetrahydro-naphthalen-2-yl)-amide; and
4'-Fluorobiphenyl-4-carboxylic acid (6-morpholin-4-ylmethyl-1,2,3,4-tetrahydro-naphthalen-2-yl)-amide.

10. A compound chosen from:
4'-Fluorobiphenyl-4-carboxylic acid (6-aminomethyl-1,2,3,4-tetrahydro-naphthalen-2-yl)-methyl-amide;
4'-Fluorobiphenyl-4-carboxylic acid (6-methylaminomethyl-1,2,3,4-tetrahydro-naphthalen-2-yl)-methyl-amide;
4'-Fluorobiphenyl-4-carboxylic acid (6-dimethylaminomethyl-1,2,3,4-tetrahydro-naphthalen-2-yl)-methyl-amide;
4'-Fluorobiphenyl-4-carboxylic acid (6-dimethylaminomethyl-1,2,3,4-tetrahydro-naphthalen-(2S)-yl)-methyl-amide;
4'-Fluorobiphenyl-4-carboxylic acid (6-ethylaminomethyl-1,2,3,4-tetrahydro-naphthalen-2-yl)-methyl-amide;
4'-Fluorobiphenyl-4-carboxylic acid (6-diethylaminomethyl-1,2,3,4-tetrahydro-naphthalen-(2R)-yl)-methyl-amide;
4'-Fluorobiphenyl-4-carboxylic acid (6-diethylaminomethyl-1,2,3,4-tetrahydro-naphthalen-(2S)-yl)-methyl-amide;
4'-Fluorobiphenyl-4-carboxylic acid (6-methyl-ethylaminomethyl-1,2,3,4-tetrahydro-naphthalen-2-yl)-methyl-amide;
4'-Fluorobiphenyl-4-carboxylic acid (6-propylaminomethyl-1,2,3,4-tetrahydro-naphthalen-2-yl)-methyl-amide;
4'-Fluorobiphenyl-4-carboxylic acid (6-dipropylaminomethyl-1,2,3,4-tetrahydro-naphthalen-2-yl)-methyl-amide;
4'-Fluorobiphenyl-4-carboxylic acid (6-isopropylaminomethyl-1,2,3,4-tetrahydro-naphthalen-2-yl)-methyl-amide;
4'-Fluorobiphenyl-4-carboxylic acid (6-diisopropylaminomethyl-1,2,3,4-tetrahydro-naphthalen-2-yl)-methyl-amide;
3',4'-DiFluorobiphenyl-4-carboxylic acid (6-dimethylaminomethyl-1,2,3,4-tetrahydro-naphthalen-(2S)-yl)-methyl amide;
3'-Trifluoromethyl-biphenyl-4-carboxylic acid (6-dimethylaminomethyl-1,2,3,4-tetrahydro-naphthalen-(2S)-yl)-methyl amide;
4'-Trifluoromethyl-biphenyl-4-carboxylic acid (6-dimethylaminomethyl-1,2,3,4-tetrahydro-naphthalen-(2S)-yl)-methyl amide;
4'-Fluorobiphenyl-4-carboxylic acid (6-piperidin-1-ylmethyl-1,2,3,4-tetrahydro-naphthalen-(2S)-yl)-methyl amide;
4'-Fluorobiphenyl-4-carboxylic acid (6-piperazin-1-ylmethyl-1,2,3,4-tetrahydro-naphthalen-(2S)-yl)-methyl amide;
4'-Fluorobiphenyl-4-carboxylic acid (6-pyrrolidin-1-ylmethyl-1,2,3,4-tetrahydro-naphthalen-(2S)-yl)-methyl amide;
4'-Fluorobiphenyl-4-carboxylic acid (6-aziridin-1-ylmethyl-1,2,3,4-tetrahydro-naphthalen-(2S)-yl)-methyl amide;
4'-Fluorobiphenyl-4-carboxylic acid (6-azepan-1-ylmethyl-1,2,3,4-tetrahydro-naphthalen-(2S)-yl)-methyl amide; and
4'-Fluorobiphenyl-4-carboxylic acid (6-morpholin-4-ylmethyl-1,2,3,4-tetrahydro-naphthalen-(2S)-yl)-methyl amide.

11. A compound chosen from:

4'-Fluorobiphenyl-4-carboxylic acid (6-diisopropylaminomethyl-1,2,3,4-tetrahydro-naphthalen-2-yl)-methyl-amide;

4'-Fluorobiphenyl-4-carboxylic acid (6-cyclohexylmethylaminomethyl-1,2,3,4-tetrahydro-naphthalen-2-yl)-methyl-amide;

4'-Fluorobiphenyl-4-carboxylic acid {6-[(2-hydroxypropylamino)methyl]-1,2,3,4-tetrahydro-naphthalen-2-yl}-methyl-amide;

4'-Fluorobiphenyl-4-carboxylic acid (6-{[(2-hydroxypropyl)methyl-amino]methyl}-1,2,3,4-tetrahydro-naphthalen-2-yl)-methyl-amide;

4'-Fluorobiphenyl-4-carboxylic acid (6-{[(2-hydroxyethyl)isopropyl-amino]methyl}-1,2,3,4-tetrahydro-naphthalen-2-yl)-methyl-amide;

4-{6-[(4'Fluorobiphenyl-4-carbonyl)methylamino]-5,6,7,8-tetrahydronaphthalen-2-ylmethyl}methylamino)butyric acid;

4-{6-[(4'Fluorobiphenyl-4-carbonyl)methylamino]-5,6,7,8-tetrahydronaphthalen-2-ylmethyl}methylamino)butyric acid methyl ester;

4-{6-[(4'Fluorobiphenyl-4-carbonyl)methylamino]-5,6,7,8-tetrahydronaphthalen-2-ylmethyl}methylamino)butyric acid dimethylamide;

4'-Trifluoromethylbiphenyl-4-carboxylic acid [6-(1-dimethylaminoethyl)-1,2,3,4-tetrahydro-naphthalen-2-yl]-methyl-amide;

4'-Trifluoromethylbiphenyl-4-carboxylic acid [6-(1-diethylaminoethyl)-1,2,3,4-tetrahydro-naphthalen-2-yl]-methyl-amide;

3',4'-Difluorobiphenyl-4-carboxylic acid [6-(1-dimethylaminoethyl)-1,2,3,4-tetrahydro-naphthalen-2-yl]-methyl-amide;

4'-Chlorobiphenyl-4-carboxylic acid [6-(1-dimethylaminoethyl)-1,2,3,4-tetrahydro-naphthalen-2-yl]-methyl-amide;

4'-Nitrobiphenyl-4-carboxylic acid [6-(1-dimethylaminoethyl)-1,2,3,4-tetrahydro-naphthalen-2-yl]-methyl-amide;

4'-Chlorobiphenyl-4-carboxylic acid [6-(2-oxa-5-azabicyclo[2.2.1]hept-5-ylmethyl)-1,2,3,4-tetrahydro-naphthalen-2-yl]-amide;

4-{6-(4'Fluorobiphenyl-4-carbonyl)methylamino]-5,6,7,8-tetrahydronaphthalen-2-ylmethyl}piperazine-1-carboxylic acid amide;

4'-Fluorobiphenyl-4-carboxylic acid [6-(3-fluoropyrrolidin-1-ylmethyl)-1,2,3,4-tetrahydro-naphthalen-2-yl]-amide;

4'-Fluorobiphenyl-4-carboxylic acid [6-(4-fluoropiperidin-1-ylmethyl)-1,2,3,4-tetrahydro-naphthalen-2-yl]-amide;

4'-Fluorobiphenyl-4-carboxylic acid [6-(4-trifluoromethyl-4-hydroxypiperidin-1-ylmethyl)-1,2,3,4-tetrahydro-naphthalen-2-yl]-amide;

4'-Fluorobiphenyl-4-carboxylic acid [6-(4-methylpiperazin-1-ylmethyl)-1,2,3,4-tetrahydro-naphthalen-2-yl]-amide;

4'-Fluorobiphenyl-4-carboxylic acid [6-(2-methoxymethylpyrrolidin-1-ylmethyl)-1,2,3,4-tetrahydro-naphthalen-2-yl]-amide;

4'-Fluorobiphenyl-4-carboxylic acid [6-(7-azabicyclo[2.2.1]hept-7-ylmethyl)-1,2,3,4-tetrahydro-naphthalen-2-yl]-amide;

4'-Fluorobiphenyl-4-carboxylic acid [6-(2-oxa-5-azabicyclo[2.2.1]hept-5-ylmethyl)-1,2,3,4-tetrahydro-naphthalen-2-yl]-amide;

4'-Fluorobiphenyl-4-carboxylic acid [6-(5-acetyl-2,5-diaza-bicyclo[2.2.1]hept-2-ylmethyl)-1,2,3,4-tetrahydro-naphthalen-2-yl]-amide;

4'-Fluorobiphenyl-4-carboxylic acid methyl-[6-(1-oxo-2,8-diaza-spiro[4.5]dec-8-ylmethyl)-1,2,3,4-tetrahydro-naphthalen-2-yl]-amide;

4'-Fluorobiphenyl-4-carboxylic acid [6-(3-hydroxypyrrolidin-1-ylmethyl)-1,2,3,4-tetrahydro-naphthalen-2-yl]-amide;

(1-{6-[(4'Fluorobiphenyl-4-carbonyl)methylamino]-5,6,7,8-tetrahydro-naphthalen-2-ylmethyl}pyrrolidine-3-yl)acetic acid;

(1-{6-[(4'Fluorobiphenyl-4-carbonyl)methylamino]-5,6,7,8-tetrahydro-naphthalen-2-ylmethyl}pyrrolidine-3-yl)acetic acid ethyl ester;

4'-Fluorobiphenyl-4-carboxylic acid [6-(3-hydroxypiperidin-1-ylmethyl)-1,2,3,4-tetrahydro-naphthalen-2-yl]-amide;

4'-Fluorobiphenyl-4-carboxylic acid [6-(4-hydroxypiperidin-1-ylmethyl)-1,2,3,4-tetrahydro-naphthalen-2-yl]-amide;

4'-Fluorobiphenyl-4-carboxylic acid [6-(4,4-difluoropiperidin-1-ylmethyl)-1,2,3,4-tetrahydro-naphthalen-2-yl]-amide; and 4-Fluorobiphenyl-4-carboxylic acid [6-(4-trifluoromethylpiperidin-1-ylmethyl)-1,2,3,4-tetrahydro-naphthalen-2-yl]-amide.

12. A pharmaceutical composition comprising:
A) an effective amount of one or more compound according to claim 1; and
B) one or more pharmaceutically acceptable excipients.

13. The compound according to claim 1 wherein $R^5$ is hydrogen.

14. A pharmaceutical composition comprising:
A) an effective amount of one or more compounds according to claim 7; and
B) one or more pharmaceutically acceptable excipients.

15. A pharmaceutical composition comprising:
A) an effective amount of one or more compounds according to claim 8; and
B) one or more pharmaceutically acceptable excipients.

16. A pharmaceutical composition comprising:
A) an effective amount of one or more compounds according to claim 9; and
B) one or more pharmaceutically acceptable excipients.

17. A pharmaceutical composition comprising:
A) an effective amount of one or more compounds according to claim 10; and
B) one or more pharmaceutically acceptable excipients.

18. A pharmaceutical composition comprising:
A) an effective amount of one or more compounds according to claim 11; and
B) one or more pharmaceutically acceptable excipients.

* * * * *

UNITED STATES PATENT AND TRADEMARK OFFICE
CERTIFICATE OF CORRECTION

PATENT NO.       : 7,304,065 B2  
APPLICATION NO.  : 10/949841  
DATED            : December 4, 2007  
INVENTOR(S)      : Xiufeng Eric Hu Page 1 of 1

It is certified that error appears in the above-identified patent and that said Letters Patent is hereby corrected as shown below:

<u>Column 17</u>
  Line 38, please delete "$CD_3OD$)" and insert -- CD3OD) --.
  Line 42, please delete "$CD_3OD$)" and insert -- CD3OD) --.

<u>Column 19</u>
  Line 16, please delete "$CD_3OD$)" and insert -- CD3OD) --.
  Line 23, please delete "$CD_3OD$)" and insert -- CD3OD) --.
  Line 48, please delete "$CD_3OD$)" and insert -- CD3OD) --.
  Line 51, please delete "$CD_3OD$)" and insert -- CD3OD) --.

<u>Column 27</u>
  Line 23, please delete "$CD_3OD$)" and insert -- CD3OD) --.
  Line 34, please delete "$CD_3OD$)" and insert -- CD3OD) --.

<u>Column 31</u>
  Line 34, please delete "from" and insert -- form --.

Signed and Sealed this

Fifth Day of August, 2008

JON W. DUDAS  
*Director of the United States Patent and Trademark Office*